United States Patent
Carmel et al.

(10) Patent No.: US 7,837,683 B2
(45) Date of Patent: Nov. 23, 2010

(54) ELECTROSURGICAL ABLATION ELECTRODE WITH ASPIRATION AND METHOD FOR USING SAME

(75) Inventors: Yuval Carmel, Rockville, MD (US); Anatoly Shkvarunets, Rockville, MD (US); Robert A. Van Wyk, Largo, FL (US)

(73) Assignee: Electrosurgery Associates, LLC, Bethesda, MD (US)

( * ) Notice: Subject to any disclaimer, the term of this patent is extended or adjusted under 35 U.S.C. 154(b) by 758 days.

(21) Appl. No.: 11/431,515

(22) Filed: May 11, 2006

(65) Prior Publication Data
US 2006/0259031 A1  Nov. 16, 2006

Related U.S. Application Data

(60) Provisional application No. 60/681,124, filed on May 13, 2005.

(51) Int. Cl.
*A61B 18/18* (2006.01)
(52) U.S. Cl. .......................... 606/41; 604/114
(58) Field of Classification Search ............. 606/23–32, 606/41–42
See application file for complete search history.

(56) References Cited

U.S. PATENT DOCUMENTS

| | | | | |
|---|---|---|---|---|
| 4,832,048 A | * | 5/1989 | Cohen | 606/41 |
| 5,681,282 A | * | 10/1997 | Eggers et al. | 604/114 |
| 6,296,638 B1 | * | 10/2001 | Davison et al. | 606/41 |
| 6,379,350 B1 | * | 4/2002 | Sharkey et al. | 606/41 |
| 6,575,968 B1 | | 6/2003 | Eggers et al. | |
| 6,589,237 B2 | * | 7/2003 | Woloszko et al. | 606/41 |
| 6,767,347 B2 | * | 7/2004 | Sharkey et al. | 606/41 |
| 6,837,884 B2 | * | 1/2005 | Woloszko | 606/32 |
| 2002/0052600 A1 | * | 5/2002 | Davison et al. | 606/41 |
| 2003/0083655 A1 | * | 5/2003 | Van Wyk | 606/41 |
| 2003/0088243 A1 | * | 5/2003 | Carmel et al. | 606/41 |
| 2004/0030330 A1 | | 2/2004 | Brassel et al. | |
| 2004/0193150 A1 | | 9/2004 | Sharkey et al. | |
| 2004/0230190 A1 | * | 11/2004 | Dahla et al. | 606/41 |
| 2005/0234446 A1 | * | 10/2005 | Van Wyk et al. | 606/41 |
| 2005/0277915 A1 | * | 12/2005 | DeCesare et al. | 606/41 |
| 2006/0259031 A1 | | 11/2006 | Carmel et al. | |

FOREIGN PATENT DOCUMENTS

WO   WO 2006/124624   11/2006

* cited by examiner

*Primary Examiner*—Linda C Dvorak
*Assistant Examiner*—Amanda Scott
(74) *Attorney, Agent, or Firm*—Chalin Smith; Smith Patent Consulting, LLC

(57) ABSTRACT

A high efficiency electrosurgical electrode with an advanced electrically conductive tip and aspiration port, and a method of conducting an electrosurgical procedure with such electrode. The electrosurgical electrode comprises an electrically conductive body portion of various geometries, an electrically conductive tip and a dielectric insulator adjacent the metallic body portion. The electrically conductive tip comprises a plurality of protuberances of various forms and geometries that define a plurality of recesses. The aspirating member includes a wall surrounding the aspirating port, to separate the aspirating port from adjacent recesses and prevent the flow of fluid from the recesses directly into the aspirating port.

25 Claims, 23 Drawing Sheets

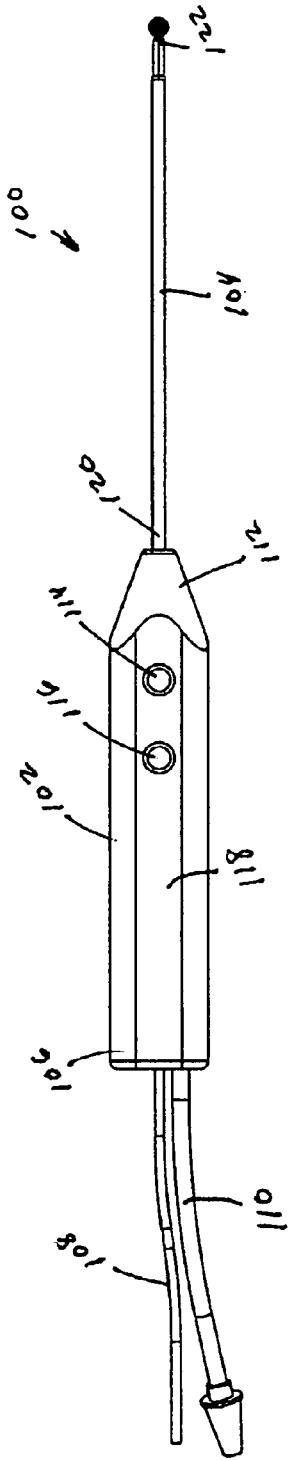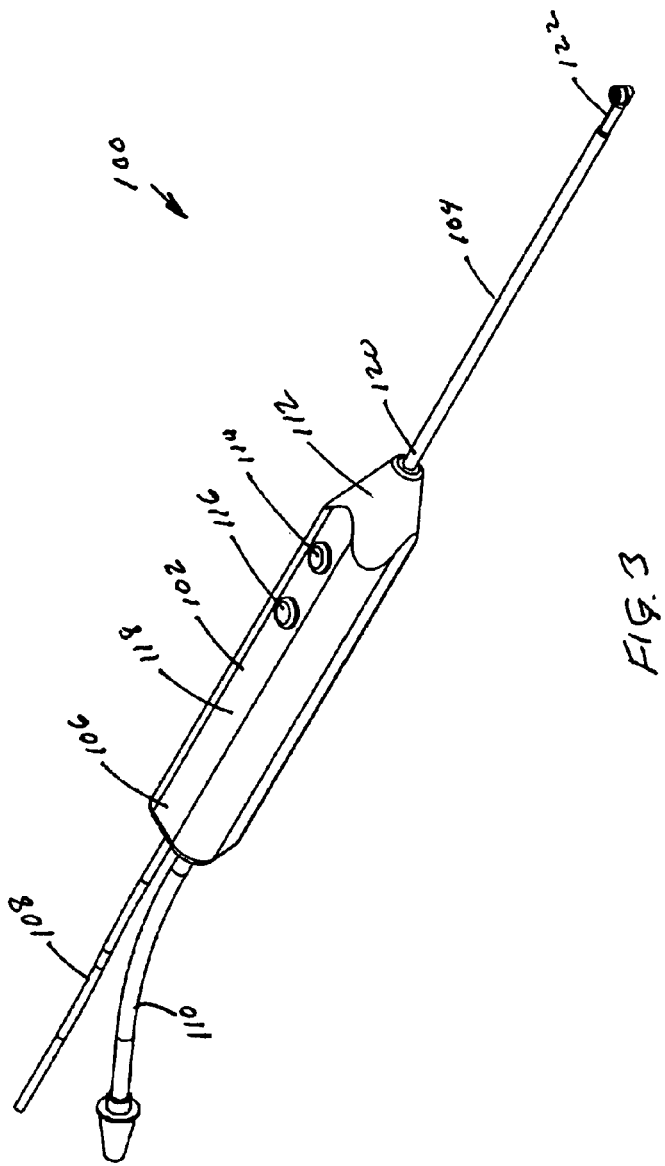
FIG. 2
FIG. 3

B-B

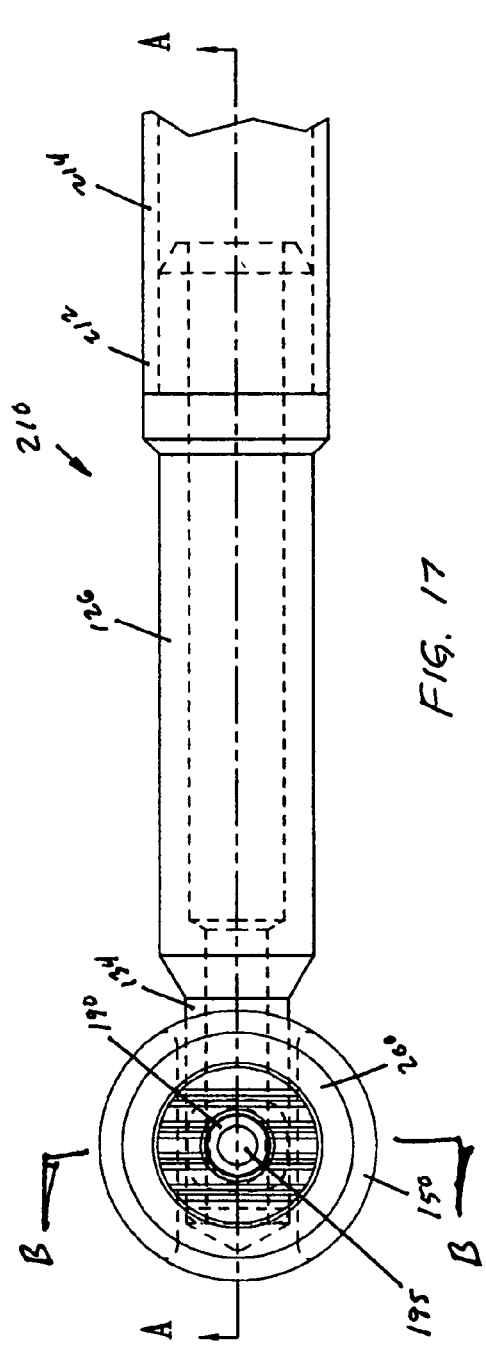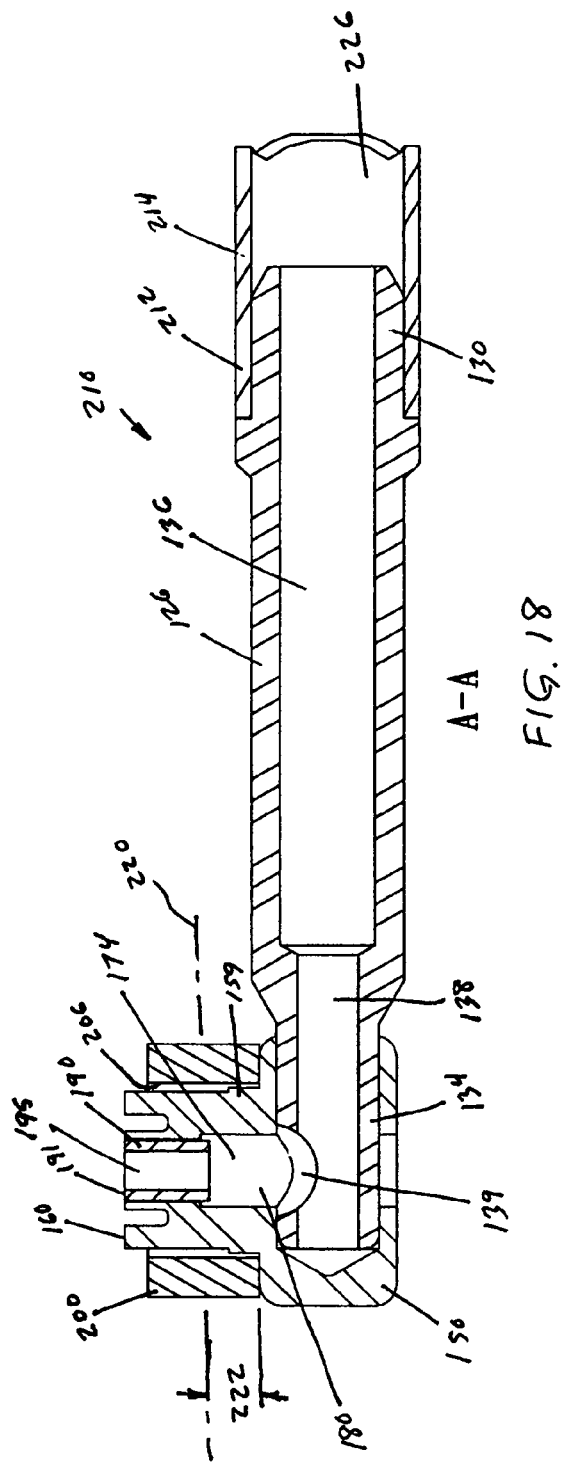

ELECTROSURGICAL ABLATION ELECTRODE WITH ASPIRATION AND METHOD FOR USING SAME

The present application claims the benefit of U.S. Provisional Application Ser. No. 60/681,124, filed on May 13, 2005, the disclosure of which is incorporated by reference herein in its entirety.

FIELD OF THE INVENTION

The present invention relates to electrosurgical devices for use in a conductive fluid environment and, more specifically, to electrosurgical devices for bulk vaporization of tissue in a conductive fluid environment which have increased efficiency through the minimization of process heat loss.

BACKGROUND OF THE INVENTION

Least invasive surgical techniques have gained significant popularity because of their ability to accomplish outcomes with reduced patient pain and accelerated return of the patient to normal activities. Arthroscopic surgery, in which the intraarticular space is filled with fluid, allows orthopedic surgeons to efficiently perform procedures using special purpose instruments designed specifically for arthroscopists. Among these special purpose tools are various manual graspers and biters, powered shaver blades and burs, and electrosurgical devices. During the last several years, specialized arthroscopic electrosurgical electrodes called ablation electrodes or ablators have been developed. Exemplary of these instruments are ArthroWands manufactured by Arthrocare (Sunnyvale, Calif.), VAPR electrodes manufactured by DePuy Mitek, a subsidiary of Johnson & Johnson (Westwood, Mass.) and electrodes by Smith and Nephew, Inc. (Andover, Mass.). These ablation electrodes differ from conventional arthroscopic electrosurgical electrodes in that they are designed for the bulk removal of tissue by vaporization, rather than the cutting of tissue or coagulation of bleeding vessels. While standard electrodes are capable of ablation, their geometries are not efficient for accomplishing this task. The tissue removal rates of ablation electrodes are lower than those of arthroscopic shaver blades, however, electrosurgical ablation electrodes or "ablators" are used because they achieve hemostasis (stop bleeding) during use and are able to efficiently remove tissue from bony surfaces. Ablation electrodes are used in an environment filled with electrically conductive fluid.

During ablation, current flow from the ablator into the conductive fluid heats the fluid to its boiling point. Heating of the conductive fluid is proportional to the density of electrical current flowing from the electrode into the fluid. Regions of high current density will experience higher rates of heating as compared to regions of low current density. Such regions of high current density typically arise at the corners and edges of the electrode. Steam bubbles form first at the edges of an ablator but eventually cover virtually the entire surface of the electrode. When a steam bubble reaches a critical size, arcing occurs within the bubble. If the bubble intersects with tissue, arcing occurs between the electrode and the tissue thereby vaporizing a portion of the tissue. A train of sparks often occurs within the bubble with the train ending when the bubble grows too large or the tissue enclosed in the bubble is evaporated, at which point conditions within the bubble become unfavorable for sparking.

During ablation, water within the target tissue is vaporized. Because volumes of tissue are vaporized rather than discretely cut out and removed from the surgical site, the power requirements for ablation electrodes are generally higher than those of other arthroscopic electrosurgical electrodes. The efficiency of the electrode design and the characteristics of the Radio Frequency (RF) power supplied to the electrode also affect the amount of power required for ablation. Electrodes with inefficient designs and/or powered by RF energy with poorly suited characteristics will require higher power levels than those with efficient designs and appropriate generators. Because of these factors, the ablation power levels of devices produced by different manufacturers vary widely with some requiring power levels significantly higher than those commonly used by arthroscopists. For example, ablation electrode systems from some manufacturers may use up to 280 Watts, significantly higher than the 30 to 70 Watt range generally required by other arthroscopic electrosurgical electrodes.

During artroscopic electrosurgery, all of the RF energy supplied to the electrode becomes heat, thereby raising the temperature of the fluid within the joint and the temperature of adjacent tissue. And, until the introduction of ablation electrodes, the temperature of the fluid within the joint was not of concern to the surgeon. However, fluid temperature is a primary concern during the use of ablation electrodes due to the higher power levels at which they generally operate and the longer periods of time that they are energized. Standard arthroscopic electrosurgical electrodes are usually energized for only brief periods, generally measured in seconds, while specific tissue is resected or modified, or a bleeder coagulated. In contrast, ablation electrodes are energized for longer periods of time, often measured in minutes, while volumes of tissue are vaporized.

The temperature of the fluid within the joint is critical since cell death occurs at 45° C., a temperature easily reached with high-powered ablators if fluid flow through the surgical site is insufficient. Patient injury can result and such injuries have been documented.

The likelihood of thermal injury is strongly affected by the amount of power supplied to the ablator. This, in turn, is determined by the efficiency of the ablator and the speed with which the surgeon desires to remove tissue. A highly efficient ablator will allow the surgeon to remove tissue at desirably high rates, while requiring low levels of power input. Under these conditions the likelihood of thermal injuries is reduced significantly.

Ablation electrodes are produced in a variety of sizes and configurations to suit a variety of procedures. For example, ablators for use in ankle, wrist or elbow arthroscopy, are smaller than those used in the knee or shoulder. In each of these sizes, a variety of configurations are produced to facilitate access to various structures within the joint being treated. These configurations differ in the working length of the electrode (i.e., the maximum distance that an electrode can be inserted into a joint), in the size and shape of their ablating surfaces and in the angle between the ablating face and the axis of the electrode shaft. Electrodes are typically designated by the angle between a normal to the ablating surface and the axis of the electrode shaft, and by the size of their ablating surface and any associated insulator.

Primary considerations of surgeons when choosing a particular configuration of ablator for a specific procedure include its convenience of use (i.e., the ease with which the instrument is able to access certain structures) and the speed with which the ablator will be able to complete the required tasks. When choosing between two configurations capable of accomplishing a task, surgeons will generally choose the ablator with the larger ablating surface so as to remove tissue more quickly. This is particularly true for procedures during which large volumes of tissue must be removed. One such procedure is acromioplasty, the reshaping of the acromion. The underside of the acromion is covered with highly vascular tissue which may bleed profusely when removed by a conventional powered cutting instrument such as an arthroscopic shaver blade. Ablation electrodes are used extensively during this procedure since they are able to remove tissue without the associated bleeding which can obscures the surgeon's view of the site. Ablation in the area under the acromion is most efficiently accomplished using an electrode on which a line normal to the ablating surface is approximately perpendicular to the axis of the ablator shaft. Such an electrode is designated as a "90 Degree Ablator" or a "side effect" ablator. Exemplary of such electrodes are the "3.2 mm 90 Degree Three-Rib UltrAblator" by Linvatec Corporation (Largo, Fla.), the "90 Degree Ablator" and "90 Degree High Profile Ablator" by Smith and Nephew (Andover, Mass.), the "Side Effect VAPR Electrode" by DePuy Mitek, a subsidiary of Johnson and Johnson, and the "3.5 mm 90 Degree Arthrowand," "3.6 mm 90 Degree Lo Pro Arthrowand," and "4.5 mm 90 Deg. Eliminator Arthrowand" by Arthrocare Corporation.

A recent improvement to ablation electrodes is the addition of means of aspiration to remove bubbles and debris from the surgical site. During electrosurgery in a conductive fluid environment, tissue is vaporized, thereby producing steam bubbles which may obscure the view of the surgeon or displace saline from the area of the intra-articular space which the surgeon wishes to affect. In the case of ablation (bulk vaporization of tissue), the number and volume of bubbles produced is even greater than when using other electrodes since fluid is continually boiling at the active electrode during use. Ideally, flow through the joint carries these bubbles away; however, in certain procedures this flow is frequently insufficient to remove all of the bubbles. The aspiration means on an aspirating ablator removes some bubbles as they are formed by the ablation process, and others after they have collected in pockets within the joint. The ablator aspiration means is connected to an external vacuum source which provides suction for bubble evacuation.

The aspiration means on currently available ablator products may be divided into two categories according to their level of flow. High-flow ablators have an aspiration tube, the axis of which is coaxial with the axis of the ablator rod or tube, which draws in bubbles and fluid through its distal opening and/or openings cut into the tube wall near its distal tip. High-flow ablators may decrease the average joint fluid temperature by removing heated saline (waste heat since it is an undesirable biproduct of the process) from the general area in which ablation is occurring. The effectiveness of the aspiration, both for removal of bubbles and for removal of waste heat, will be affected by the distance between the opening through which aspiration is accomplished and the active electrode. The distal tip of the aspiration tube is generally several millimeters distant proximally from the active electrode so as to not to obstruct the surgeon's view of the electrode during use. Decreasing this distance is desirable since doing so will increase the effectiveness of the aspiration. However, this must be accomplished without limiting the surgeon's view or decreasing the ablator's ability to access certain structures during use. Examples of high-flow aspirating ablators systems include the Three Rib-Aspirating ablators by Linvatec Corporation and the 2.3 mm and 3.5 mm Suction Sheaths for the VAPR system by DePuy Mitek, the sheaths being used with standard VAPR ablation probes.

Arthrex, Inc. (Naples, Fla.) markets aspirating ablators having an aspiration means wherein the aspiration port is in the distal-most surface of the device, and the aspiration path is through the device. These devices have higher flow rates than low-flow ablators, though less than the high-flow models previously herein described.

Low-flow ablators are those which aspirate bubbles and fluid through gaps in the ablating surfaces of the active electrode and convey them from the surgical site via means in the elongated distal portion of the device. Current low-flow ablators require increased power to operate as effectively as a nonaspirating or high-flow aspirating ablators because the low-flow aspiration is drawing hot saline from the active site of a thermal process. In the case of low-flow ablators, the heat removed is necessary process heat rather than the waste heat removed by high-flow ablators. Because of this, aspirating ablators of the low-flow type generally require higher power levels to operate than other ablators thereby generating more waste heat and increasing undesirable heating of the fluid within the joint. Typical of low-flow aspirating ablators are those produced by Arthrocare and Smith and Nephew.

Each of these types of aspirating ablation electrodes has its drawbacks. In the case of high-flow aspirating ablators, the aspiration tube increases the diameter of the device thereby necessitating the use of larger cannulae, which, in turn, results in an increase in wound size and often an increase in patient pain and recovery time. In the case of low-flow aspirating ablators, the devices decrease the efficiency of the probes since process heat is removed from a thermal process. This decreased efficiency results in decreased rates of tissue removal for a given power level. This results in increased procedure times or necessitates the use of higher power levels to achieve satisfactory tissue removal rates. High power levels are undesirable as they cause increased heating of the fluid at the site and thereby increase the likelihood of thermal injury to the patient.

It is an object of this invention to produce an electrosurgical ablation electrode which aspirates through the ablating portion of the active electrode and has increased ablation efficiency as compared to existing ablation electrodes which aspirate through the active electrode.

SUMMARY OF THE INVENTION

The present invention provides an aspirating electrosurgical ablator for use in a conductive fluid environment, and which has a means for directing aspiration flow so that the loss of process heat is minimized. In one embodiment, the means for directing aspiration flow comprises a tubular member which draws fluid preferentially from the region distal to (above) the active electrode, and which reduces fluid flow through the spaces between protuberances of the active electrode adjacent the tubular member. The tubular member may be integral with the active electrode or provided as a separate component.

The present invention also provides an electrosurgical ablator with increased efficiency in an electrosurgical procedure. The method comprises the steps of: (i) positioning an electrosurgical probe adjacent a target tissue, the electrosurgical probe comprising a means for directing aspiration flow to minimize the loss of process heat; and (ii) either submerging the target tissue in an electrical conducting fluid or (iii) directing an electrically conducting fluid to the target tissue to ablate tissue in the region adjacent the means for directing aspiration flow.

These and other features and advantages of the present invention will become more fully apparent from the following description of the invention which refers to the accompanying drawings. However, it is to be understood that both the foregoing summary of the invention and the following detailed description are of illustrative and preferred embodiments, and should not be construed as restrictive of the present invention or other alternate embodiments. For example, although the present invention is described herein in the context of arthroscopy, the invention is not so limited. Rather, the present invention is equally applicable to other procedures that involve the application of high frequency electrical power to cut, vaporize, ablate, coagulate and/or treat a body tissue, cavity or vessel in a conductive fluid environment. Furthermore, in addition to the ablative procedures discussed in detail herein, the electrosurgical devices of the present invention also find utility in the context of thermal treatments, lesion formation, tissue sculpting and the like.

BRIEF DESCRIPTION OF THE DRAWINGS

FIG. 2 is a plan view of an electrosurgical ablator constructed in accordance with the principles of this invention.

FIG. 3 is a perspective view of the objects of FIG. 2.

FIG. 17 is a plan view of the distal end assembly of the object of FIG. 2.

FIG. 18 is a side elevational sectional view of the objects of FIG. 17 at location A-A of FIG. 17.

DETAILED DESCRIPTION OF THE PREFERRED EMBODIMENTS

The present invention provides an electrosurgical probe with an electrosurgical electrode having means for directing aspiration flow so that the loss of process heat is minimized and being capable of achieving high ablation rates at low RF power levels.

Figure 1:
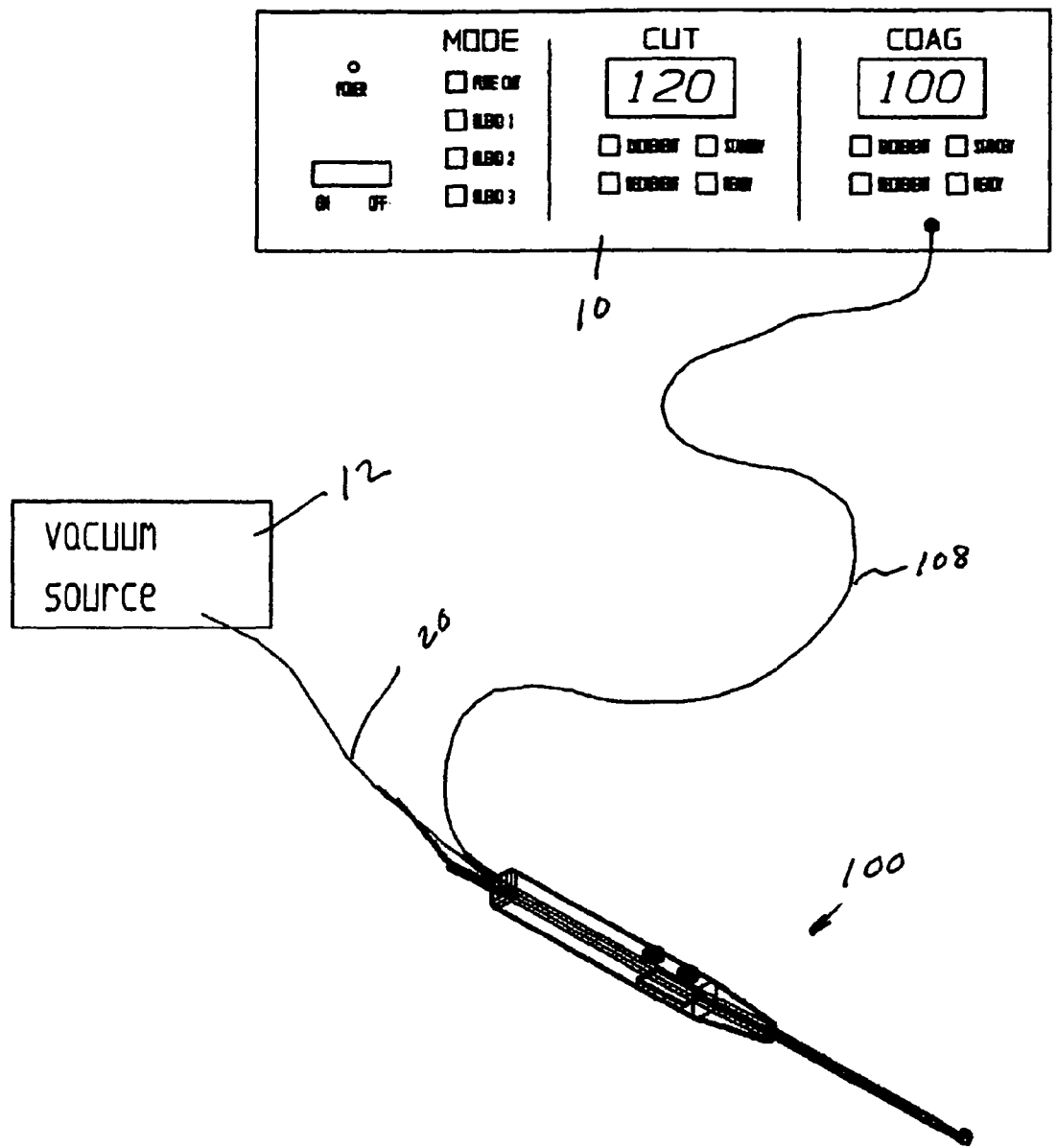
FIG. 1 is a schematic representation of the electrosurgical system according to the principles of this invention.
Figure 4:
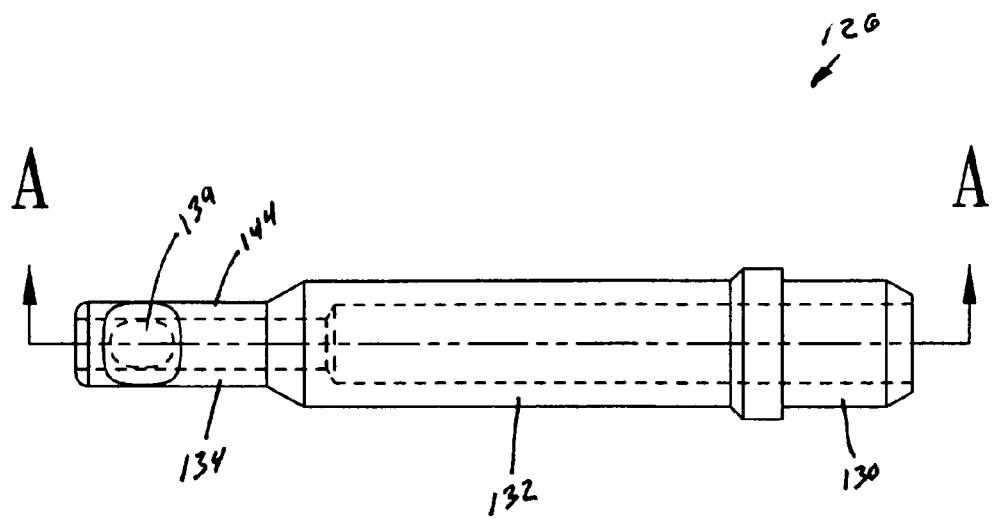
FIG. 4 is a plan view of the mandrel component of the object of FIG. 2.
Figure 5:
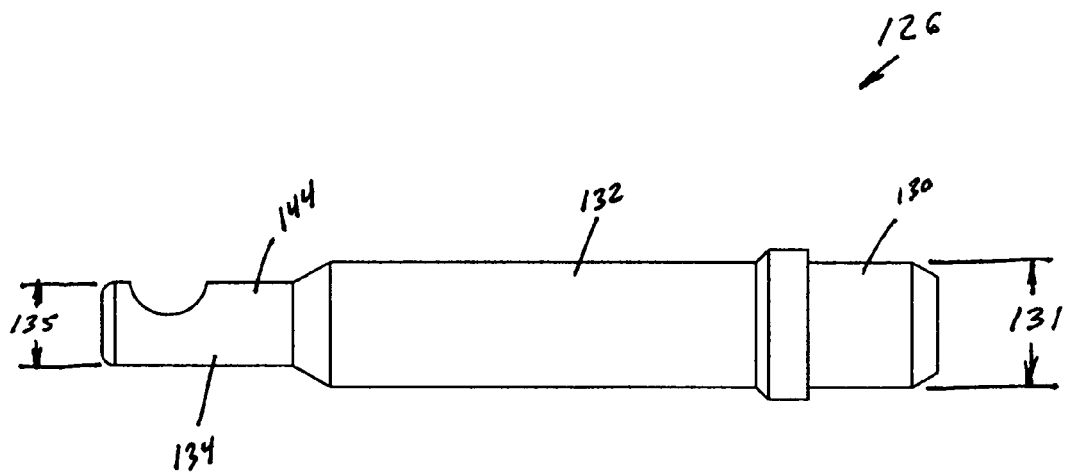
FIG. 5 is a side elevational view of the object of FIG. 4.
Figure 6:
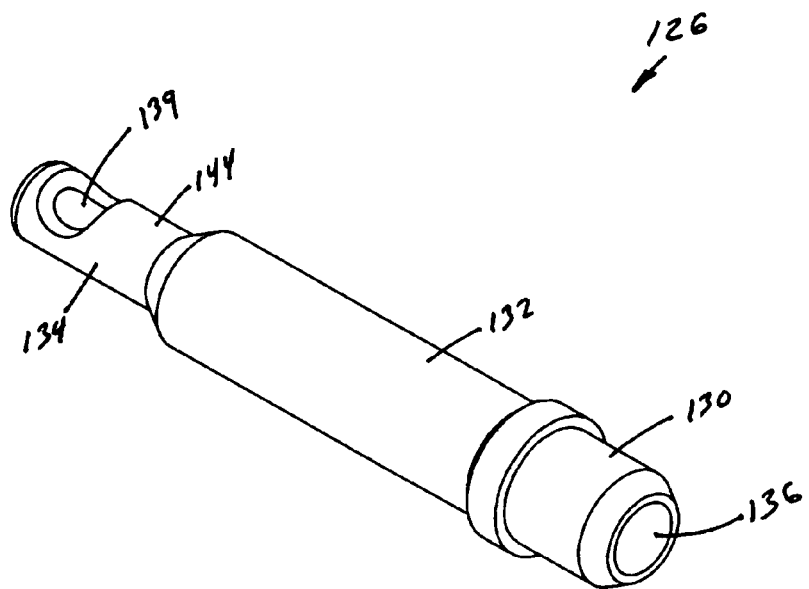
FIG. 6 is a perspective view of the object of FIG. 4.

Referring now to the drawings, where like elements are designated by like reference numerals, FIG. 1 depicts an electrosurgery system constructed in accordance with the principles of this invention. Ablation electrode 100 is connected by electrical cable 108 to electrosurgical generator 10, and by tube 120 to an external vacuum source 12. A return electrode (not shown) is connected to the electrosurgical generator to provide a return path for the RF energy. The return electrode may be a dispersive pad attached to the patient at a site remote from the surgical site, or may be in proximity to the active electrode in contact with tissue or the conductive liquid.

Reference is now made to FIGS. 2 and 3, which illustrate an electrosurgical instrument 100 constructed in accordance with the principles of this invention. Instrument 100, also called an ablation electrode, "ablator" or "probe," has a proximal portion 102 forming a handle and an elongated distal portion 104. Handle 102 has passing from its proximal end 106 electrical cable 108 which is connected to electrosurgical generator 10, and flexible tube 110 which is connected to tube 120 and thereby to external vacuum source 12. Near distal end 112 of handle 102, first activation button 114 labeled "ablate" and second activation button 116 labeled "coagulate," protrude from top surface 118 of handle 102. Elongated distal portion 104 has a proximal end 120 which is mounted to distal end 112 of handle 102, and a distal end 122.

Referring now to FIGS. 4 through 7, mandrel 126 has a proximal portion 130 of diameter 131, a mid-portion 132 and a distal portion 134 of diameter 135, and a lumen having a proximal portion 136 extending through proximal portion 130 and mid-portion 132, and a distal lumen portion 138 within distal portion 134 of mandrel 126. Passage 139 extends from outer surface 144 of distal portion 134 to distal lumen portion 138. Mandrel 126 is made from a suitable metallic material, examples of which include, but are not limited to, stainless steel, nickel, titanium or tungsten, and equivalents thereof.

Figure 7:
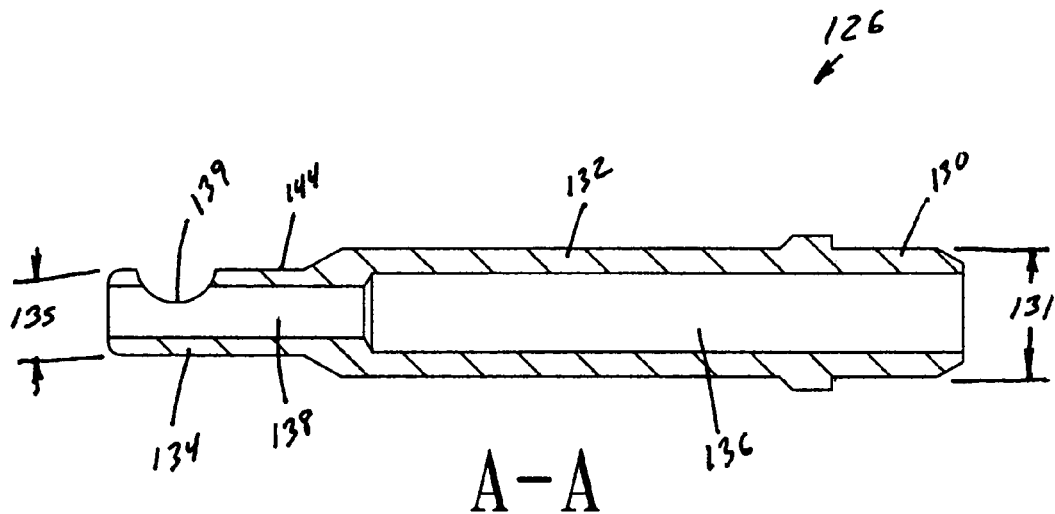
FIG. 7 is a side elevational sectional view of the object of FIG. 2 at location A-A of FIG. 2.
Figure 8:
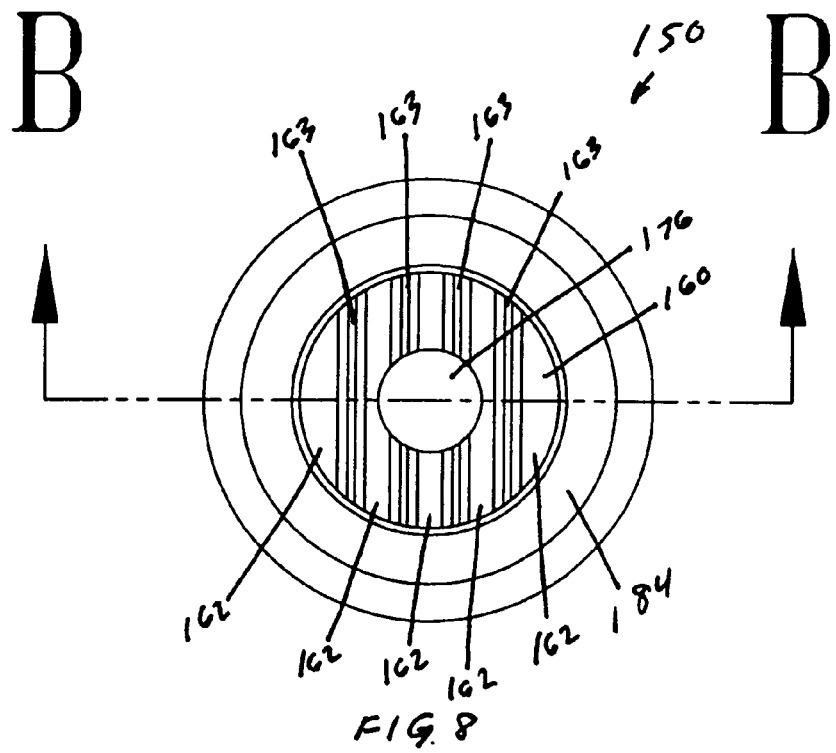
FIG. 8 is a plan view of the active electrode component of the object of FIG. 2.

As seen in FIGS. 8 through 12, electrode piece 150 has an upper portion 156 of diameter 158, with an upper surface 160 in which are formed a series of elevated protuberances or ribs 162 that define a plurality of corresponding recessed grooves or channels 163, and a mid-portion 159 of diameter 161. Piece 150 also has a lower portion 164 (a body region) of diameter 166 in which is formed cylindrical radial passage 168 of diameter 170 and depth 172. Lumen 174, coaxial with upper portion 156 and lower portion 164, has an upper portion 176 of diameter 178 and a lower portion 180 of diameter 182. Lower portion 180 intersects radial passage 168. Top surface 184 of lower portion 164 forms a shelf. Beveled surfaces 186 are parallel to axis 188 of passage 168. Diameter 170 of radial passage 168 is slightly less than diameter 135 of distal portion 134 of mandrel 126 (FIG. 7).

Electrode piece 150 may be made from a suitable electrically conductive material, examples of which include, but not limited to, metals such as stainless steel, nickel, titanium and tungsten, among many others, or an electrically conductive ceramic. The body region of the electrode piece 150 may have various cross-sectional shapes and geometries, including, but not limited to, cylindrical, rectangular, or ellipsoidal, among many others. When viewed in side elevation as in FIGS. 9 and 11, protuberances or ribs 162 and corresponding recessed grooves 163 may also have various geometries and/or shapes and various cross-sections, including, but not limited to, rectangular trapezoidal, triangular, square, hexagonal, round, and ellipsoidal, among many others.

Figure 11:
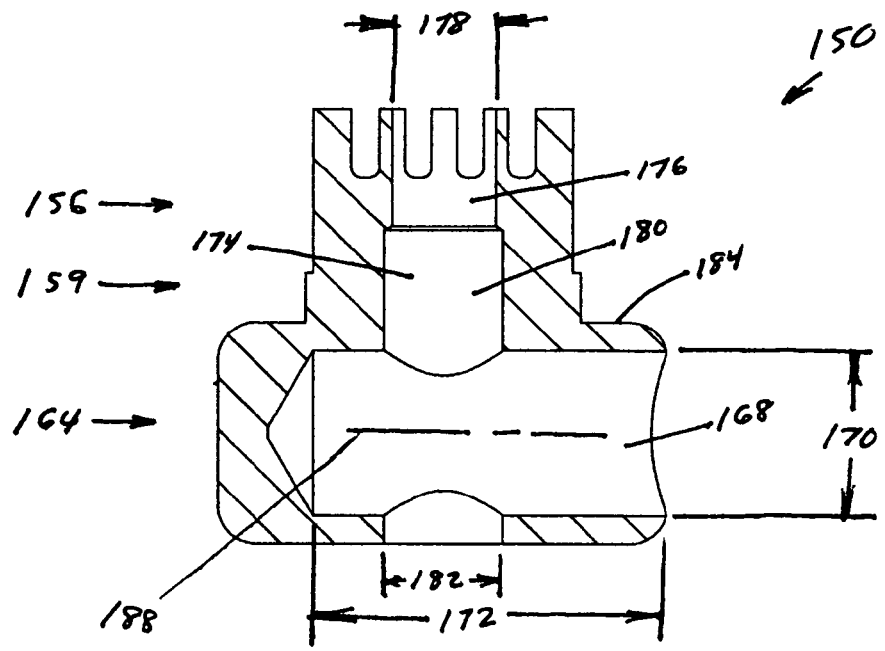
FIG. 11 is a side elevational sectional view of the object of FIG. 8 at location B-B of FIG. 8.
Figure 12:
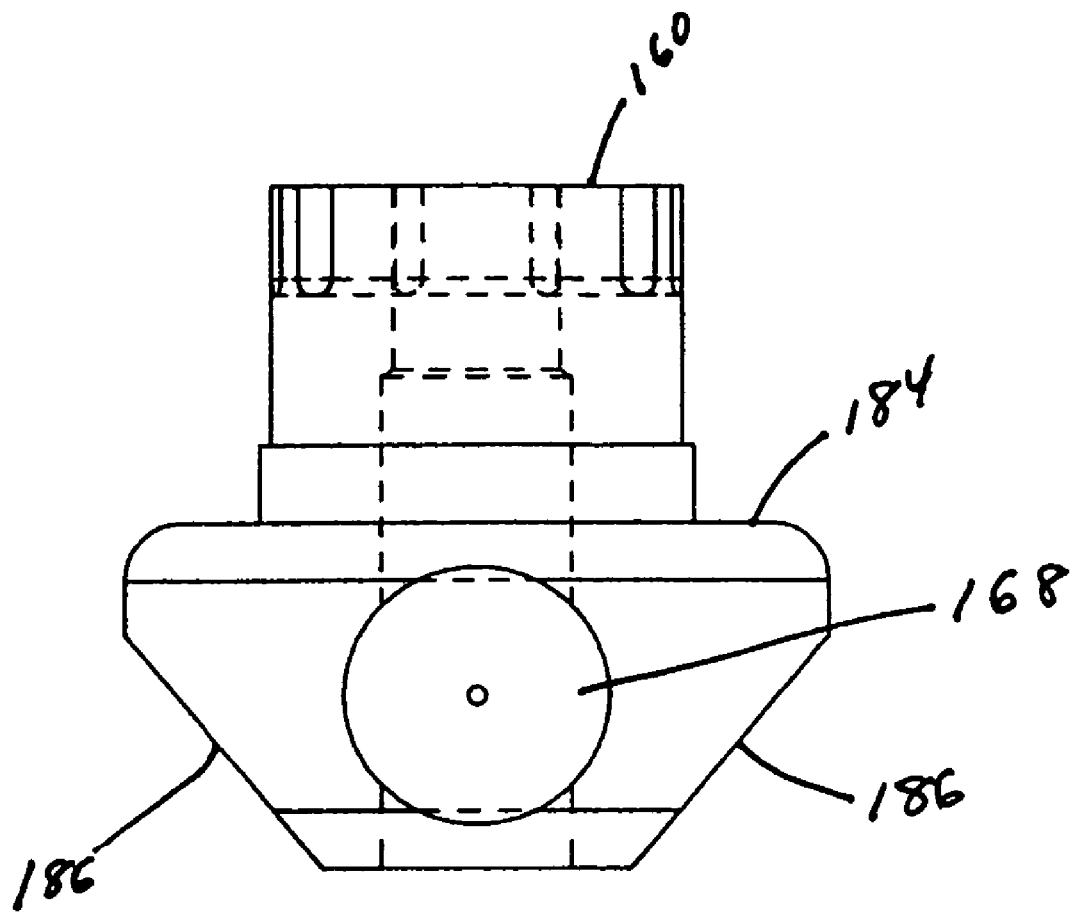
FIG. 12 is a proximal axial view of the object of FIG. 8.
Figure 13:
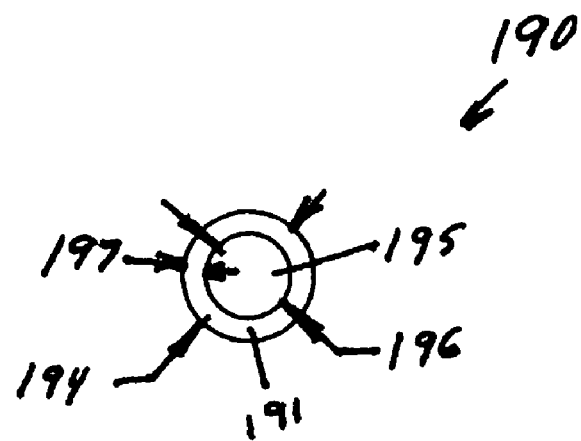
FIG. 13 is a plan view of the aspiration tube component of the object of FIG. 2.
Figure 14:
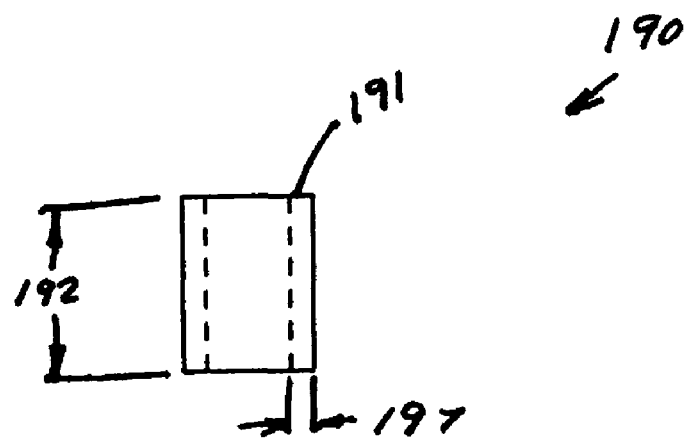
FIG. 14 is a side elevational view of the object of FIG. 13.

FIGS. 13 and 14 depict aspiration means 190 of length 192. In an exemplary embodiment, the aspiration means 190 is an aspiration tube having an outer diameter 194 and a lumen 195 of diameter 196. The wall thickness 197 of aspiration tube 190 is preferably between about 0.08 mm to about 1.5 mm, and more preferably between about 0.1 mm to about 0.6 mm. Diameter 194 is slightly larger than diameter 178 of upper portion 176 of lumen 174 of electrode piece 150 (FIG. 11).

Aspiration tube 190 may be made from a suitable electrically conductive material including, but not limited to, metallic material such as, for example, stainless steel, nickel, titanium or tungsten, or alternatively from a ceramic materials such as alumina or zirconia. In yet other embodiments, the aspiration tube 190 may comprise a combination of at least a metallic material and at least a ceramic material. Although reference to the aspiration means is made in this application as to an "aspiration tube," the invention contemplates any aspirating member having various shapes and different cross-sections when viewed in plan view. For example, lumen 195 may be round (FIG. 13), but the outer shape may have a rectangular cross-section, a square, a hexagonal, or an ellipsoidal shape, among many others. The wall thickness 197 of the aspiration member may be constant (as for aspiration tube 190), or may vary depending on the lumen and outer shape cross-sections. As noted above, the thickness 197 of aspiration tube 190 is preferably between about 0.08 mm to about 1.5 mm, and more preferably between about 0.1 mm to about 0.6 mm. In exemplary embodiments, the aspiration member may be provided as a separate component, or constructed integral with the active electrode (as a one-piece assembly, for example).

Figure 9:
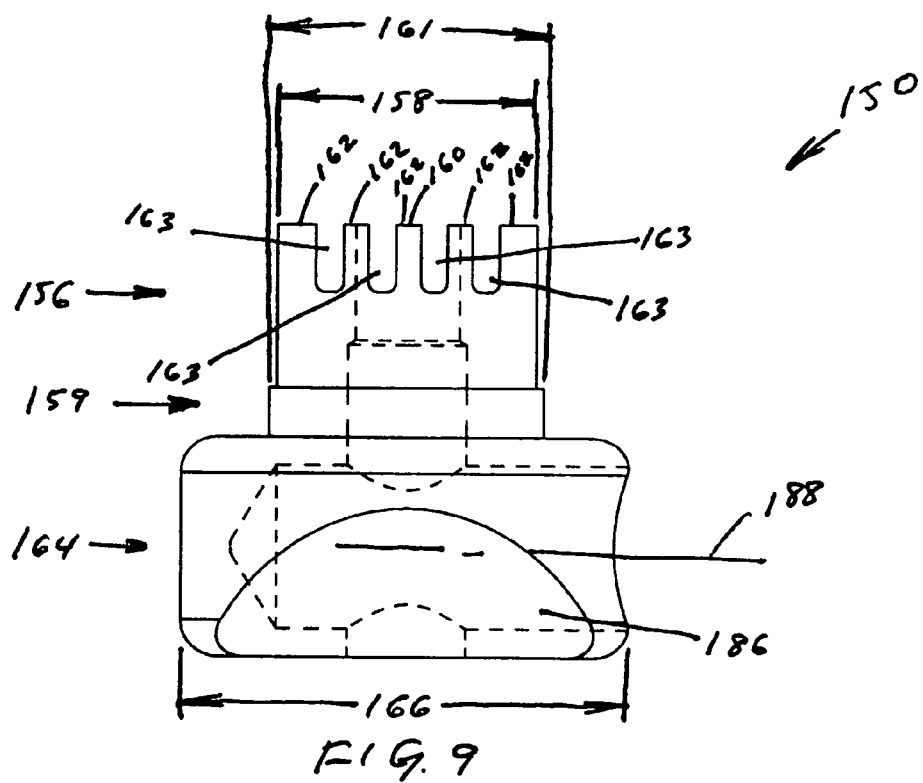
FIG. 9 is a side elevational view of the object of FIG. 8.
Figure 10:
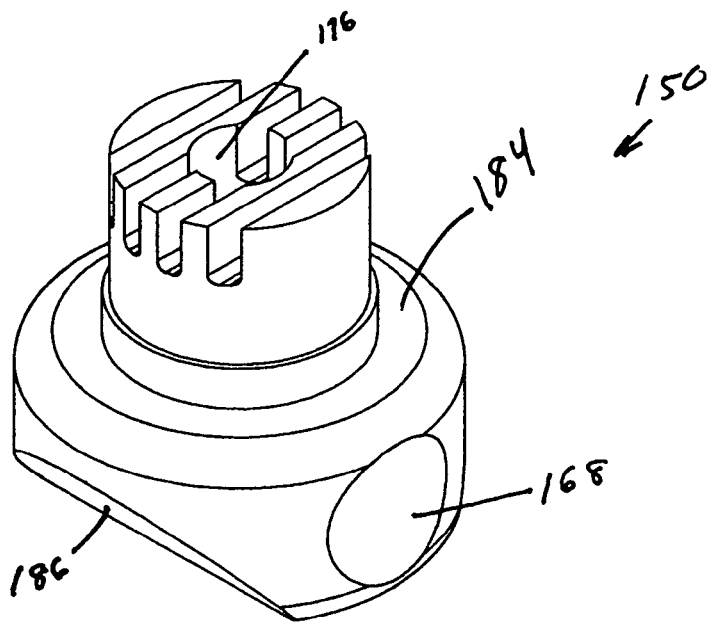
FIG. 10 is a perspective view of the object of FIG. 8.
Figure 15:
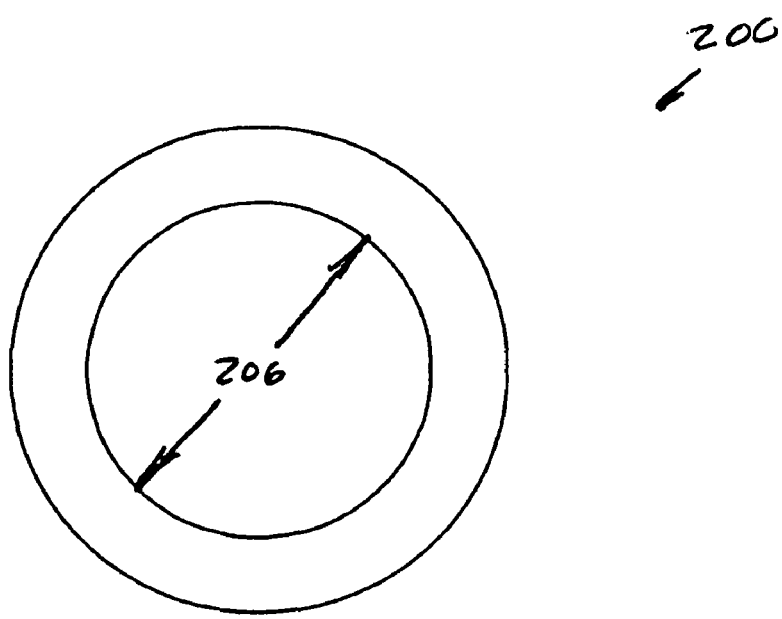
FIG. 15 is a plan view of the insulator component of the object of FIG. 2.
Figure 16:
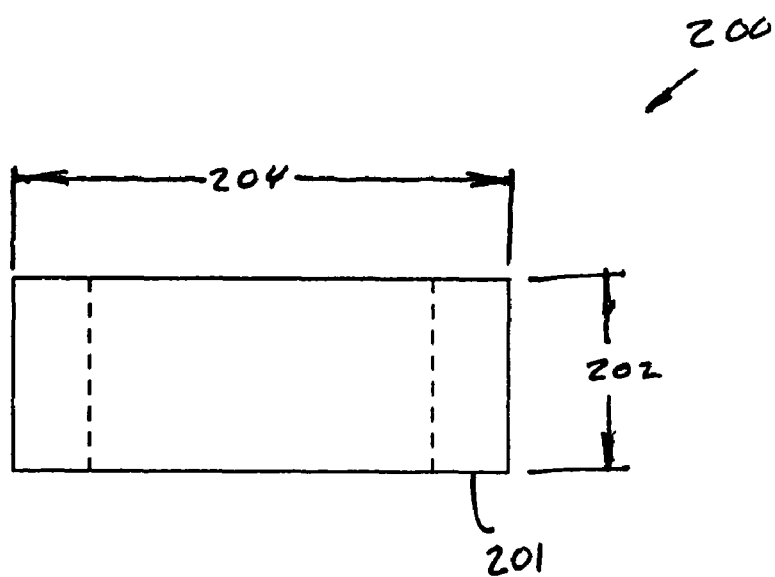
FIG. 16 is a side elevational view of the object of FIG. 15.
Figure 19:
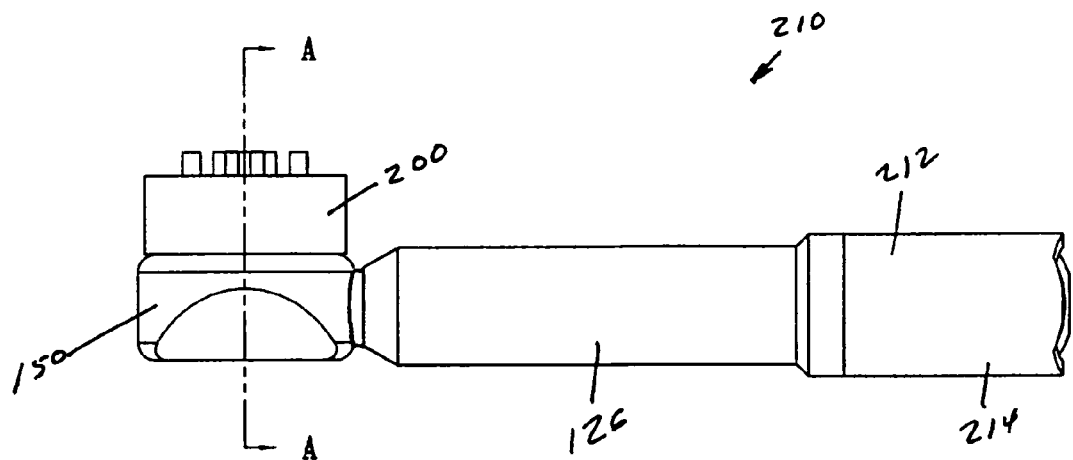
FIG. 19 is a side elevational view of the objects of FIG. 17.
Figure 20:
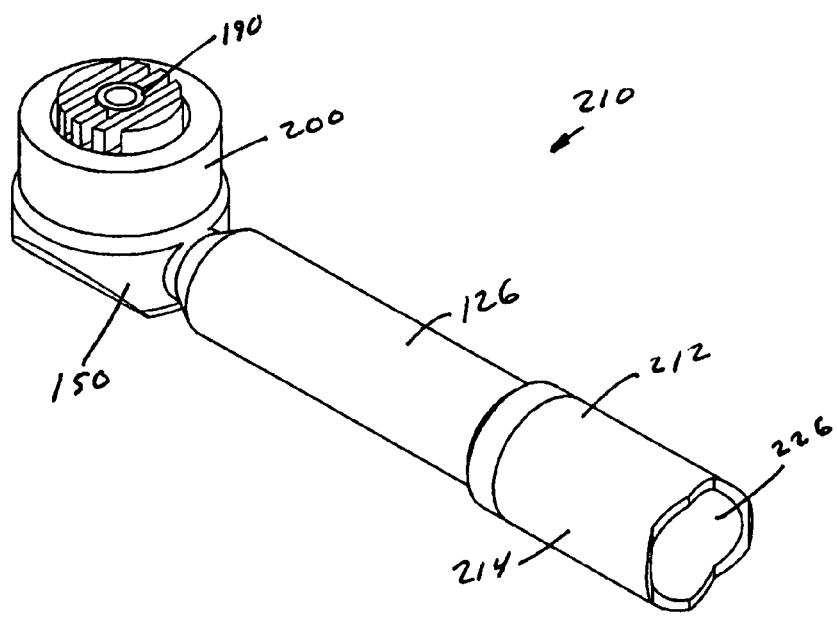
FIG. 20 is a perspective view of the objects of FIG. 17.
Figure 21:
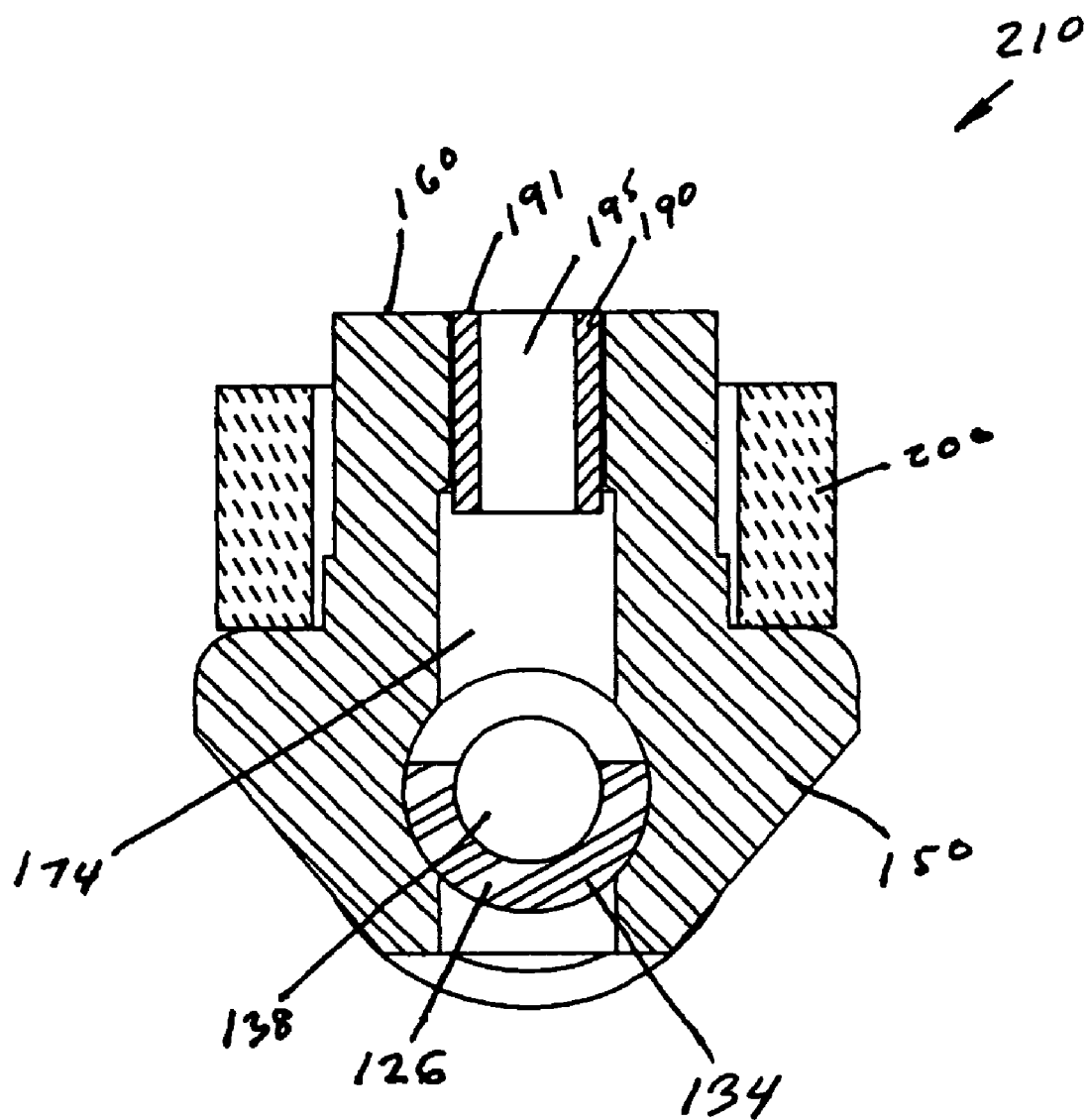
FIG. 21 is an axial sectional view of the objects of FIG. 17 at location B-B of FIG. 17.

As seen in FIGS. 15 and 16, insulator 200 of height 202 and outer diameter 204 has a cylindrical inner lumen of diameter 206. Diameter 206 is slightly larger than diameter 161 of mid-portion 159 of electrode piece 150 (FIG. 9). Insulator 200 has a bottom surface 201. Insulator 200 is made from a suitable dielectric material such as alumina or zirconia, or a high-temperature polymeric material.

Referring to FIGS. 17 through 21 showing distal end assembly 210, aspiration tube 190 is provided as a component separate from the electrode piece 150. According to an exemplary embodiment, aspiration tube 190 is pressed into upper portion 176 of lumen 174 (FIG. 11) such that top end surface 191 of tube 190 is coplanar with surface 160 of electrode piece 150. Electrode piece 150 is assembled to mandrel 126, distal portion 134 of mandrel 126 being pressed into radial passage 168 of electrode 150 (FIG. 11) such that passage 139 of mandrel 126 is aligned with lower portion 180 of lumen 174 of piece 150. Proximal portion 130 of mandrel 126 (FIG. 7) is assembled to distal end 212 of tube 214, tube 214 extending proximally from assembly 210 to handle 102. Insulator 200 is assembled to electrode piece 150, bottom surface 201 of insulator 200 (FIG. 16) resting on shelf 184 of piece 150 (FIGS. 10 and 11), and mid-portion 159 of piece 150 being within lumen 206 of insulator 200 so that insulator 200 is coaxial with upper portion 156 of electrode piece 150. A dielectric coating (not shown) covers elongated distal portion 104 from handle 102 to line 220 at a distance 222 above shelf 184 and bottom surface 201 of insulator 200.

Figure 22:
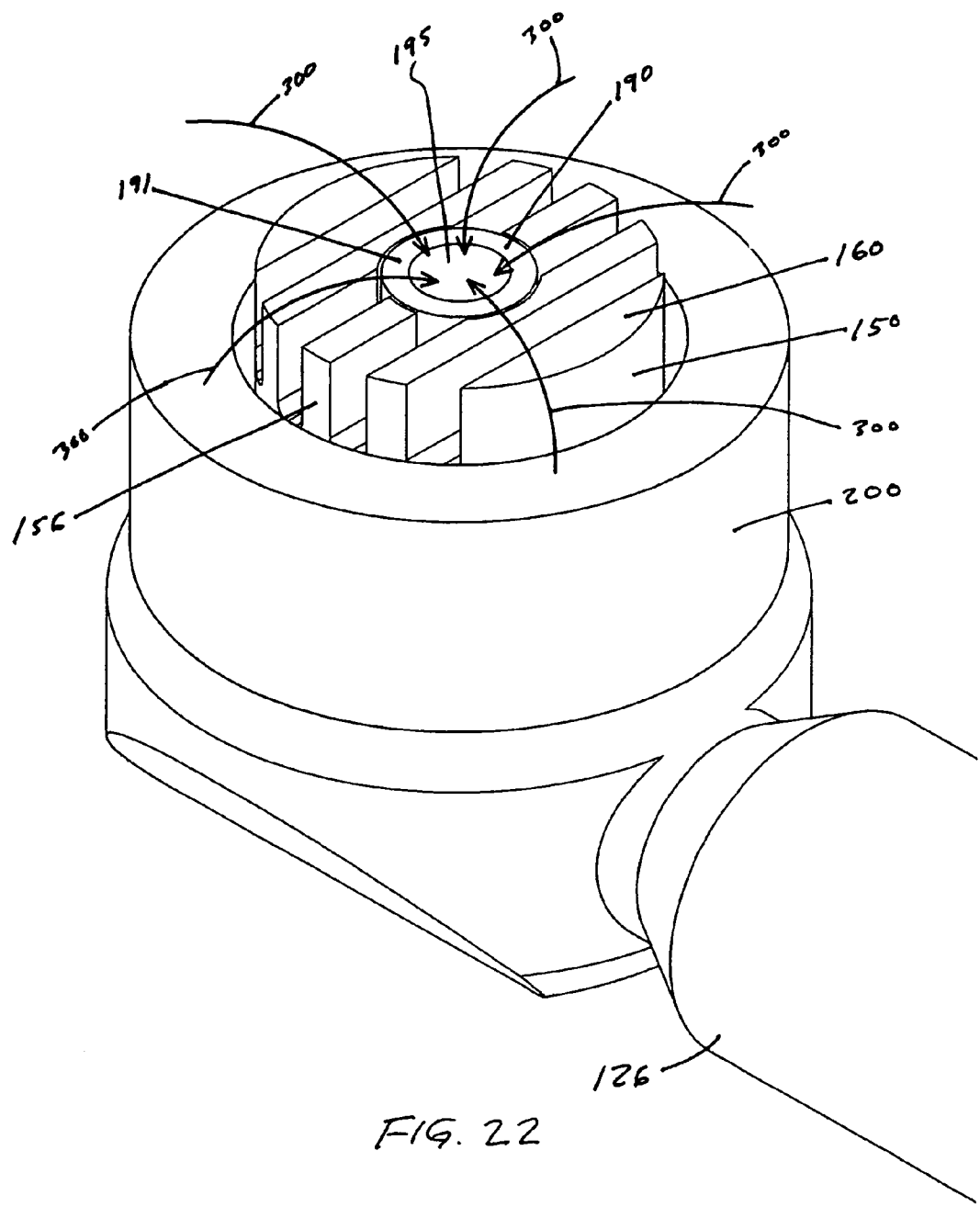
FIG. 22 is an expanded perspective view of the ablating surface of the active electrode showing aspiration flow.

Lumen 195 of aspiration tube 190, lumen 174 of electrode piece 150, passage 139, distal lumen portion 138 and proximal lumen portion 136 of mandrel 126, and lumen 226 of tube 214 together form a flow path in communication via means within handle 102 with flexible tube 110 which is connected to external vacuum source 12. During use, with the probe distal end 122 submerged in conductive liquid and with a vacuum applied to the flow path, liquid 300 is aspirated from the from the site as shown in FIG. 22, particularly from the region distal to (above) surface 160 of electrode 150, and surface 191 of aspiration tube 190.

Figure 23:
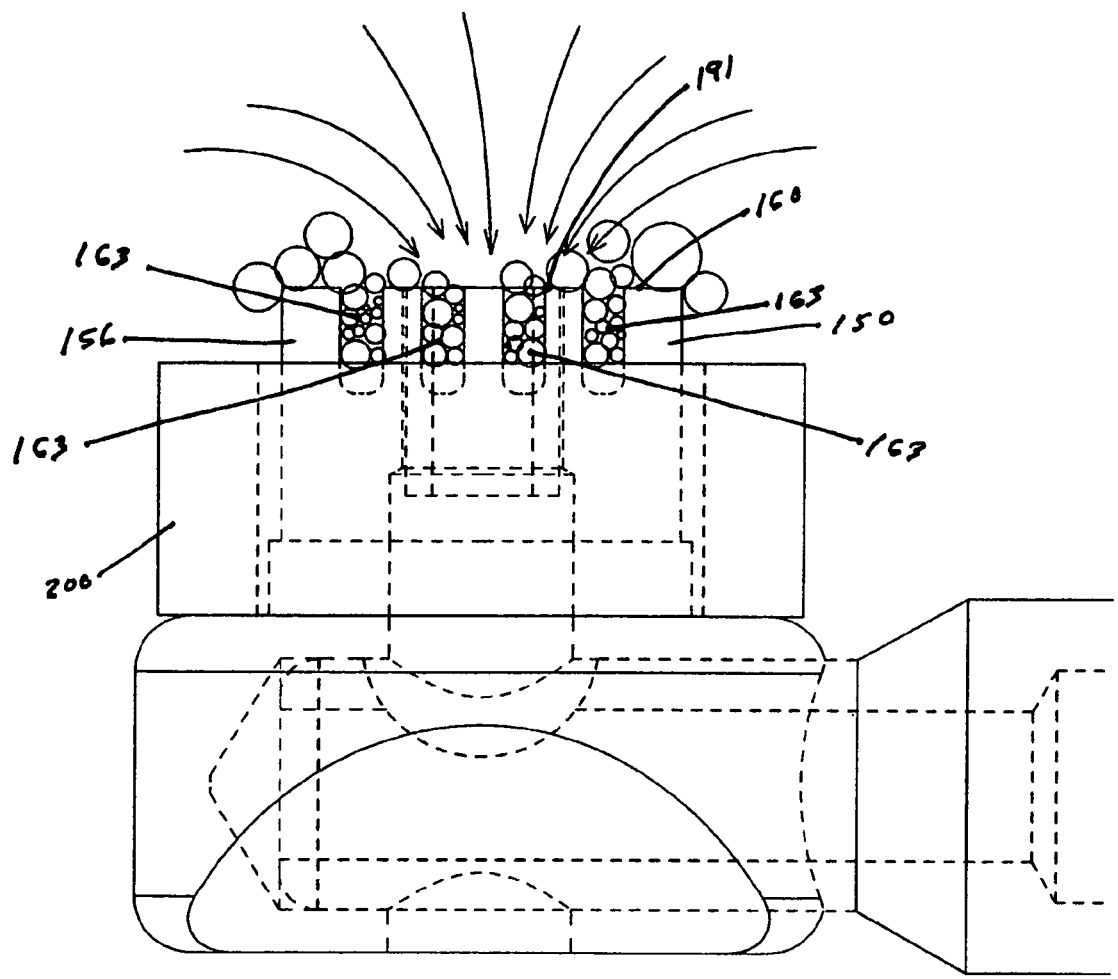
FIG. 23 is an expanded side elevational view of the distal portion of the objects of FIG. 16 during use showing bubble formation.

Referring now to FIG. 23, radio frequency (RF) energy is supplied to active electrode 150 creating an electric field in the conductive fluid. Current flows into the conductive fluid from the portion of active electrode upper portion 156 protruding above insulator 200. Current flowing through the liquid heats the fluid, making it more conductive, which in turn causes more current to flow through the heated region. Heating of the conductive liquid in this region causes it to boil so as to form bubbles at active electrode 150. These bubbles form at surface 160 of ribs 162, and in grooves 163. Bubbles filling grooves 163 insulate the surfaces of the grooves thereby decreasing current flow from these surfaces.

Bubbles forming at surface 160 and in portions of the ribs adjacent thereto grow to a critical size whereupon arcing occurs within some of these bubbles. When distal end 122 of ablator 100 is brought into close proximity to tissue, some of the bubbles intersect the tissue and arcing occurs between active electrode 150 and the tissue resulting in vaporization (ablation) of tissue.

Figure 24:
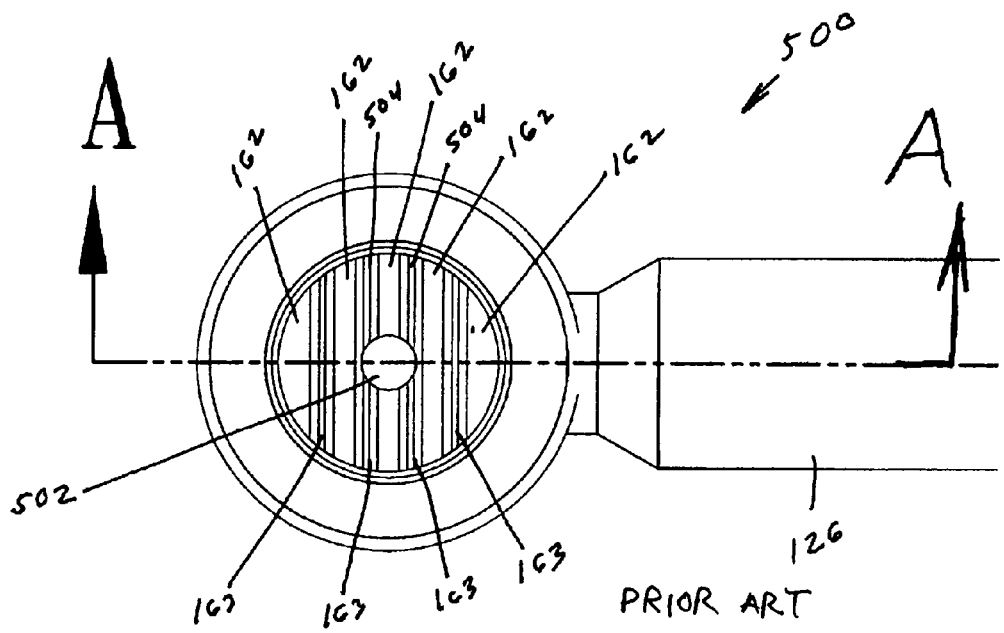
FIG. 24 is an expanded plan view of the distal portion of a prior art device.
Figure 25:
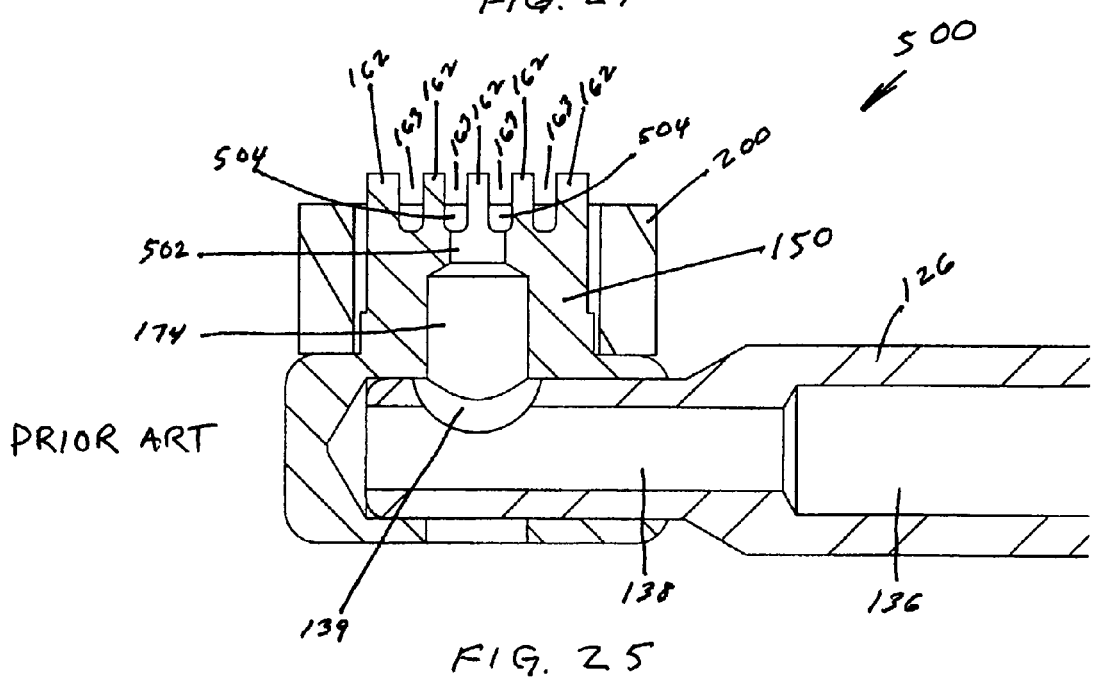
FIG. 25 is a side elevational sectional view of the objects of FIG. 24 at location A-A of FIG. 24.
Figure 26:
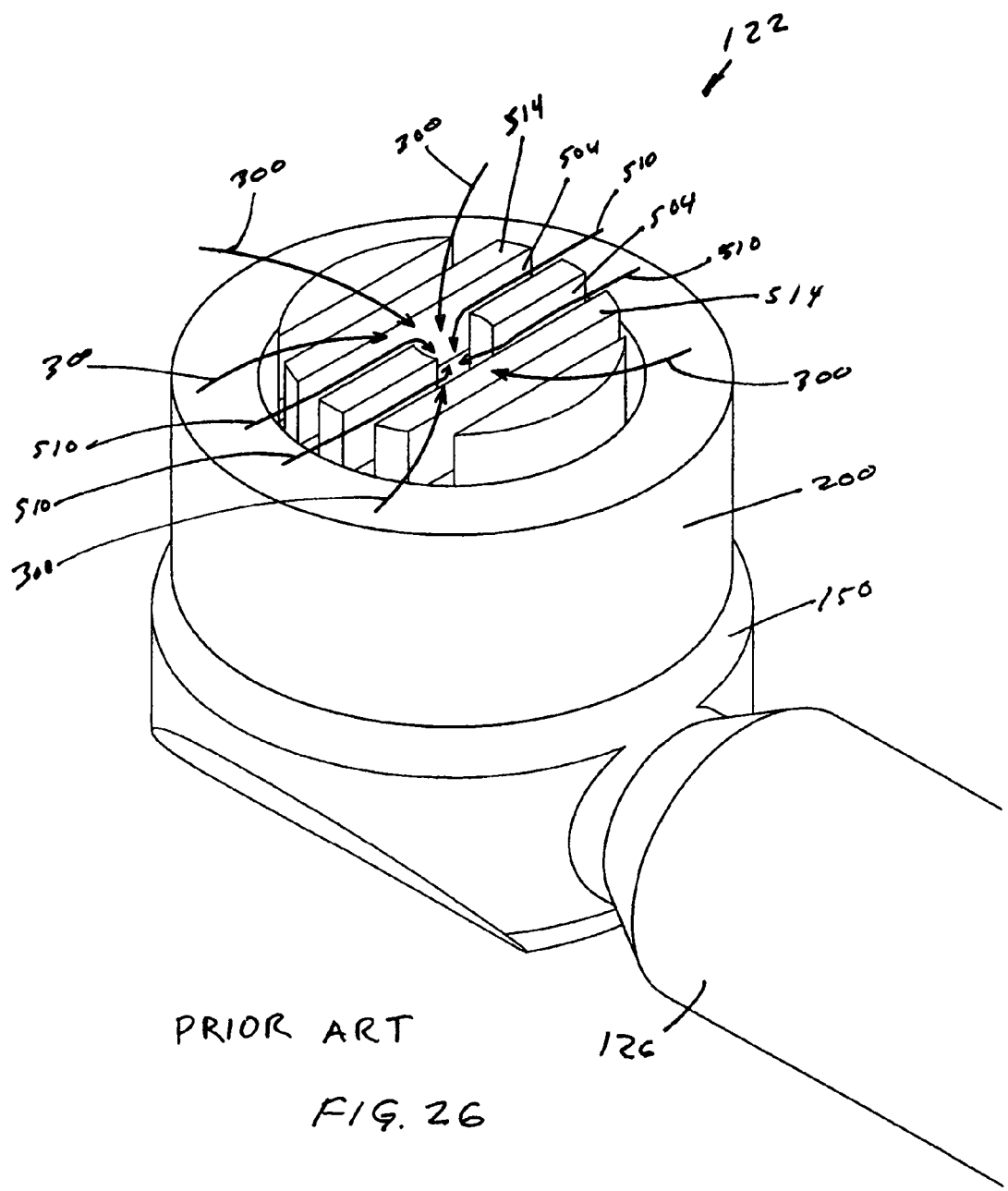
FIG. 26 is an expanded perspective view of the ablating surface of the objects of FIG. 24 during use showing the aspiration flow.

The beneficial effect of aspiration tube 190 is best understood by considering the operation of a prior art ablation electrode 500 similar to ablator 100, with the exception that aspiration tube 190 is absent. Referring now to FIGS. 24 and 25 which depict the distal portion of prior art device 500, active electrode piece 150 has a lumen 502 of the same diameter as lumen 195 of aspiration tube 190 (FIG. 13). Lumen 502 intersects medial grooves 504. Lumen 502, lumen 174 of electrode piece 150, passage 139, distal lumen portion 138 and proximal lumen portion 136 of mandrel 126, and lumen 226 of tube 214 together form a flow path in communication via means within handle 102 with flexible tube 110 which is connected to external vacuum source 12. During use, with the probe distal end 122 submerged in conductive liquid and with a vacuum applied to the flow path, liquid 300 is aspirated from the site as shown in FIG. 26, from the region distal to (above) surface 160 of electrode 150, and (referring to flow paths 510) from medial grooves 504.

Figure 27:
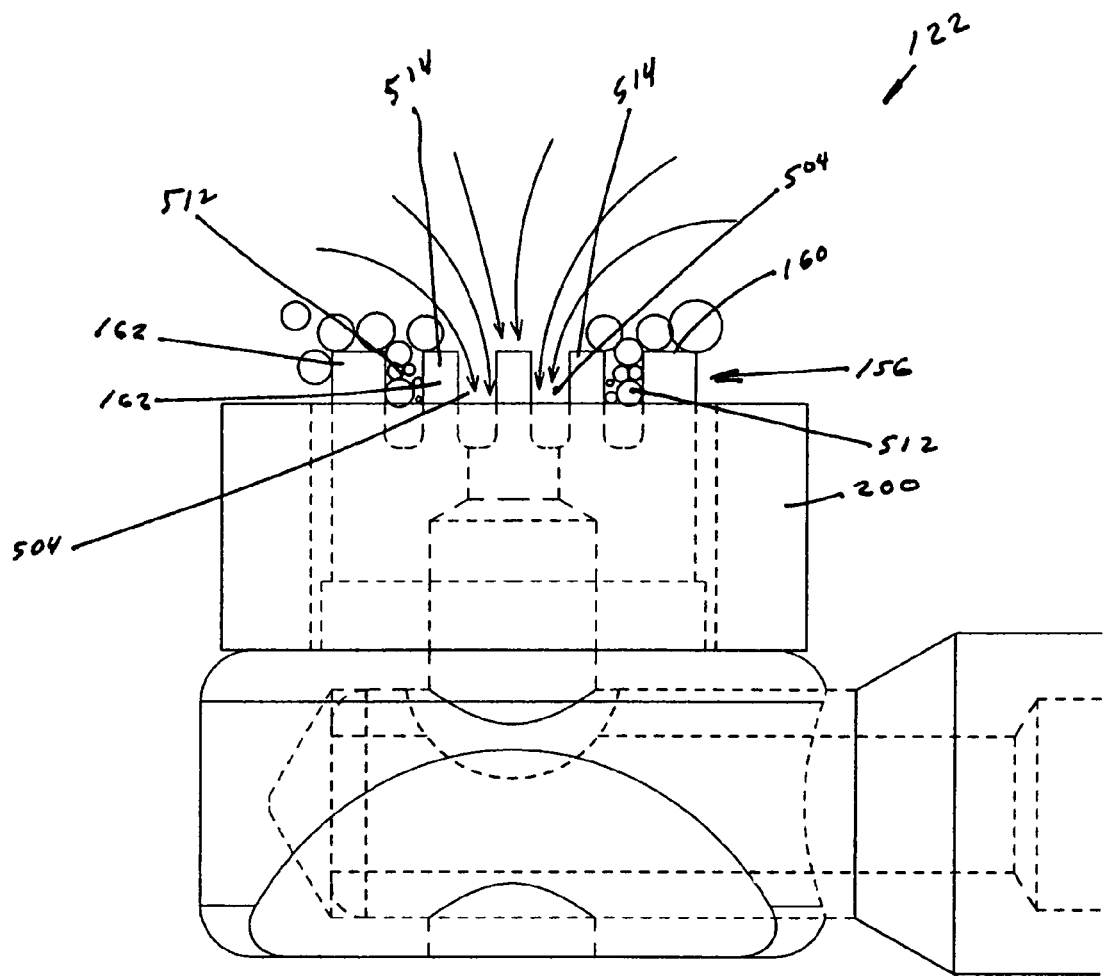
FIG. 27 is an expanded side elevational view of the distal portion of the objects of FIG. 24 during use showing bubble formation.

Radio Frequency (RF) energy is supplied to active electrode 150 creating an electric field in the conductive fluid. Current flows into the conductive fluid from the portion of active electrode upper portion 156 protruding above insulator 200. Current flowing through the liquid heats the fluid, making it more conductive, which in turn causes more current to flow through the heated region. Referring to FIG. 27, heating of the conductive liquid in this region causes it to boil forming bubbles at active electrode 150. These bubbles form at surface 160 of ribs 162, and in lateral grooves 512. Flow 510 in medial grooves 504 carries the heat away from these regions thereby preventing fluid therein from boiling. Because medial grooves 504 do not fill with bubbles so as to insulate the grooves' surfaces, current flows from the surfaces to the conductive fluid in contact therewith so as to heat the fluid which is then aspirated from the region providing no clinical benefit to the patient. Ribs 514 adjacent to medial ribs 504 are also cooled by flow 510 which decreases bubble production on these ribs. Accordingly, the number of bubbles produced by the ablator, and therefore the number of bubbles which grow to critical size, create arcing and vaporize tissue is decreased. This, in turn, results in decreased efficiency. The power applied to the electrode must be increased to achieve tissue removal rates comparable to those of an ablator produced in accordance with the principles of this invention.

Figure 28:
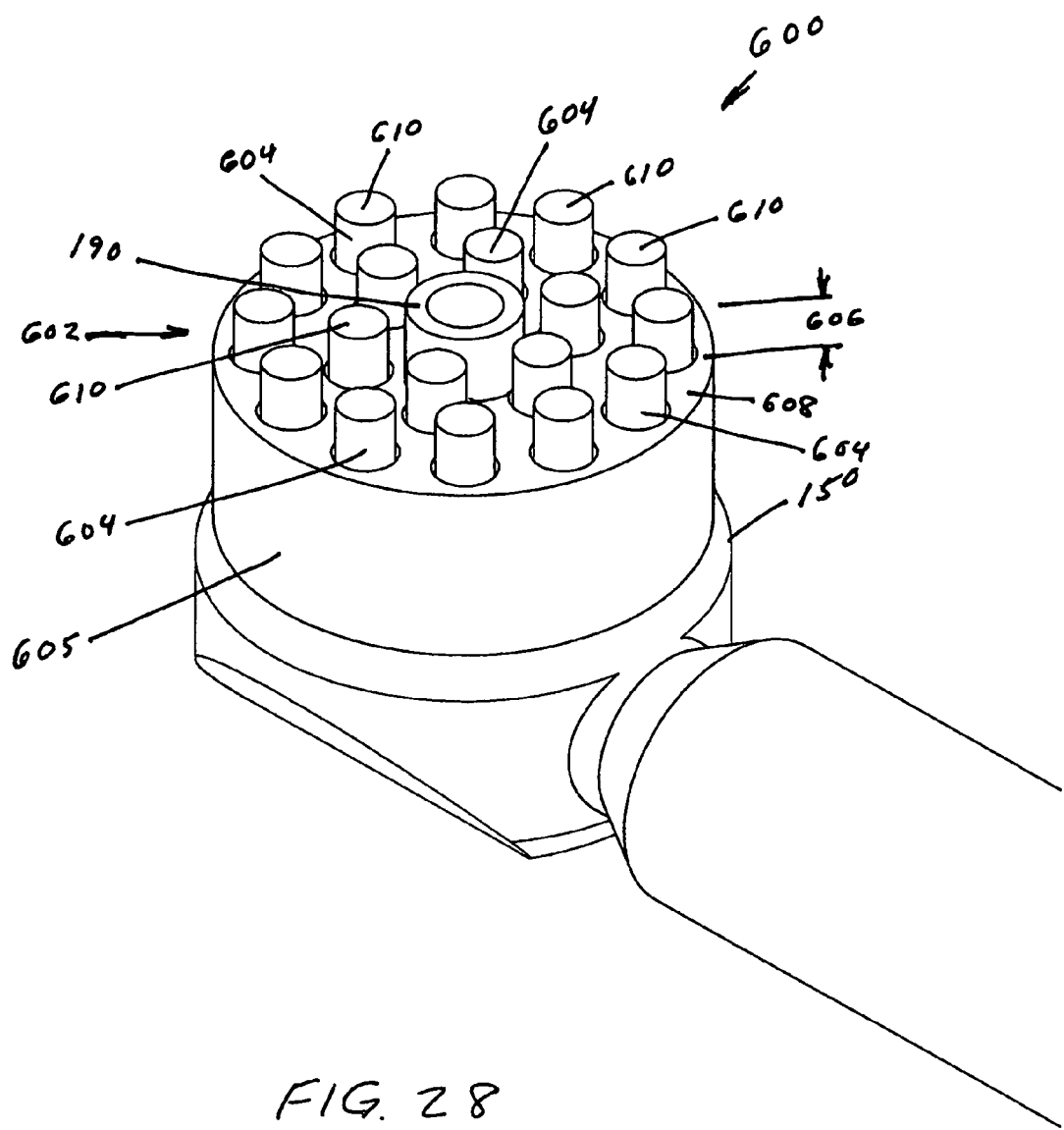
FIG. 28 is an expanded perspective view of the distal portion of the distal assembly of an alternate embodiment.

The principles of this invention may be advantageously applied to ablator electrodes having active electrodes with ablating surfaces which are not ribbed but rather include protuberances of other shapes. That is, the present invention contemplates the addition of an aspirating member according to the principles of this invention of any ablation electrode so as to minimize cooling flow around the active elements and thereby increase the efficiency of the probe. For instance, aspirating ablating electrode 600, the distal portion of which is shown in FIG. 28, is similar in construction to the previous embodiment, except that electrode 150 has an upper portion 602 which forms cylindrical protuberances 604 which protrude through passages in ceramic insulator 605, to a height 606 above surface 608 of insulator 605. These elevated protuberances define a plurality of recessed "channels" therebetween, such "channels" being analogous to the linear "grooves" of previous embodiments. Aspiration tube 190 protrudes above surface 608 of insulator 605 approximately distance 606. As with the previous embodiment, aspiration tube 190 causes fluid aspiration primarily from the region distal to (above) distal ends 610 of protuberances 604. Protuberances 604 have a circular shape when viewed in a plan view. In other embodiments, protuberances 604 may have other shapes when viewed in a plan view including ellipsoidal, for example, or regularly or irregularly polygonal, or a combination of such regularly or irregularly polygonal shapes. The cross-sections may be constant or alternatively, may vary with height.

Figure 29:
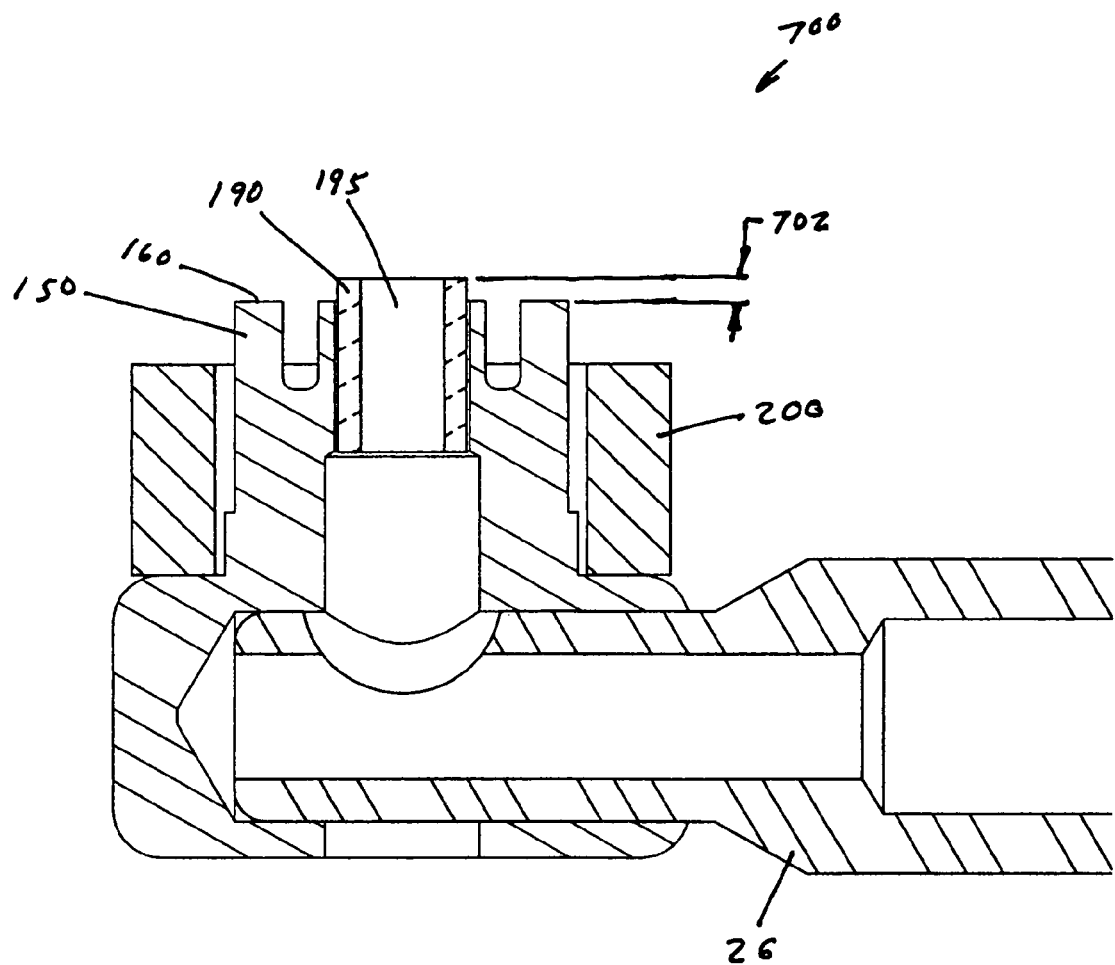
FIG. 29 is an expanded side elevational sectional view of the distal portion of the distal assembly of an alternate embodiment.

The increase in efficiency of an ablator electrode through the incorporation of an aspirating member according to the principles of this invention is determined by the degree of reduction of the flow between protuberances of the active electrode. This, in turn, is determined by the height of the aspirating member relative to the height of the protuberances. In embodiments described above, the height of aspirating member 190 is about equal to the height of the protuberances on the active electrode face. In other embodiments contemplated by the present invention, member 190 may have a height that is less than the height of the protuberances. In these exemplary embodiments, the cooling flow between the protuberances will be reduced but not eliminated, as in previous embodiments having aspirating members equal in height to the protuberances. This reduced flow will increase the efficiency of the ablator since the removal of process heat is decreased compared to the same aspirating electrode without an aspirating member of the present invention. It may be desirable in some embodiments to aspirate liquid from regions farther removed distally from the ablating surface of the active electrode. Referring to FIG. 29 showing the distal portion of an ablator 700, aspirating tube 190 protrudes beyond surface 160 of active electrode 150 by a distance 702. The distance or height 702 is preferably between about 0.1 mm to about 3 mm, and more preferably between about 0.1 mm to about 2 mm.

Figure 30:
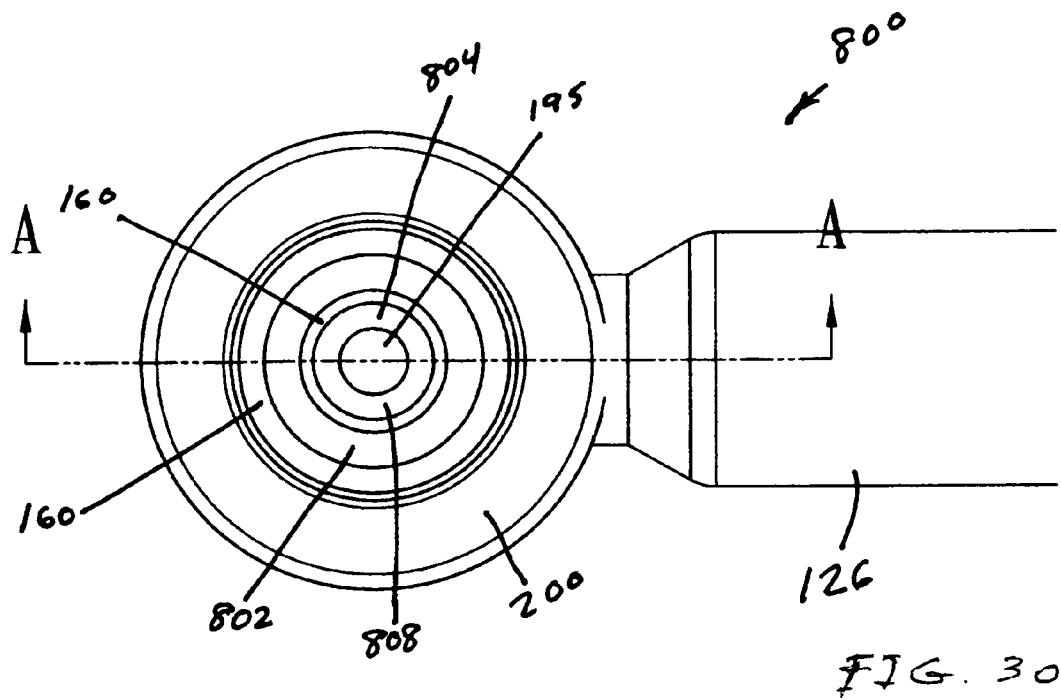
FIG. 30 is an expanded plan view of the distal portion of an alternate embodiment formed in accordance with the principles of this invention.
Figure 31:
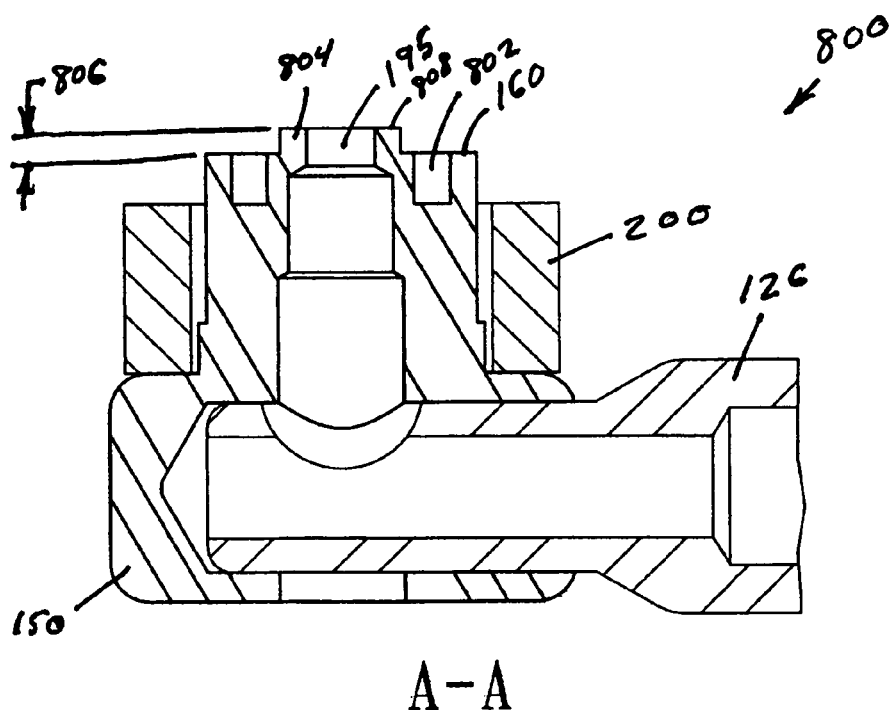
FIG. 31 is a side elevational sectional view of the objects of FIG. 30 at location A-A of FIG. 30.
Figure 32:
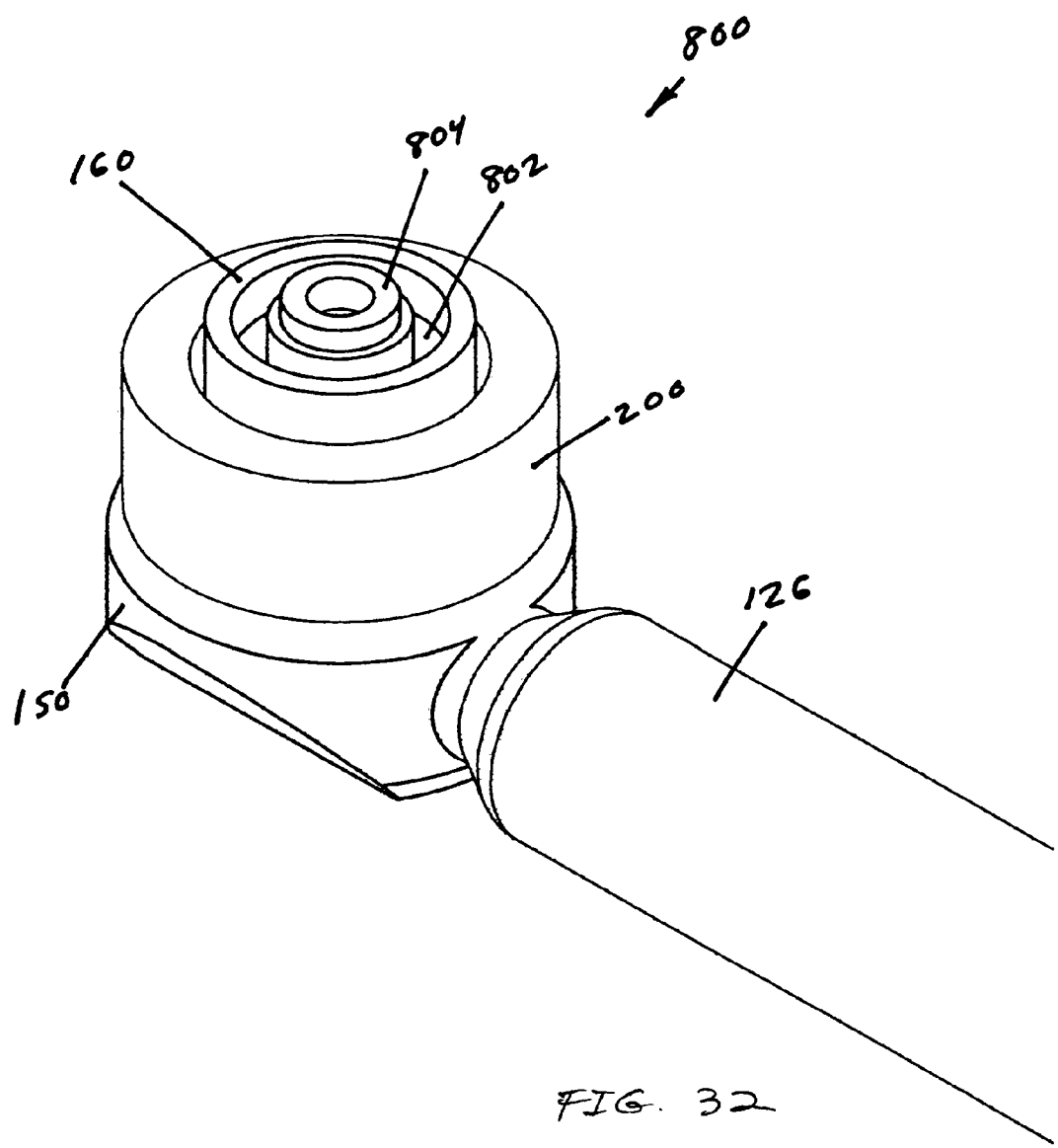
FIG. 32 is a perspective view of the objects of FIG. 30.

In yet another embodiment, at least one circular groove is formed in the ablating surface, the at least one groove being concentric with the aspiration port. Referring now to FIGS. 30 through 32, showing the distal portion of an ablator 800, groove 802 is concentric with aspirating lumen 195. As shown in FIG. 31, tubular portion 804 of active electrode 150 has replaced aspiration tube 190 of previous embodiments. Surface 808 of portion 804 protrudes distance 806 beyond surface 160 of active electrode 150. Because groove 802 does not intersect lumen 195, cooling of adjacent rib surfaces by aspiration flow is prevented. Tubular portion 804 of active electrode 150 protrudes beyond surface 160 of electrode 150 so as to increase the efficiency of ablator 800 by decreasing cooling caused by liquid flow across surfaces 160. In other embodiments, surface 808 of portion 804 is coplanar with surface 160. In yet other embodiments having larger diameter ablating surfaces, additional circular grooves 802 are formed in active electrode 150.

Figure 34:
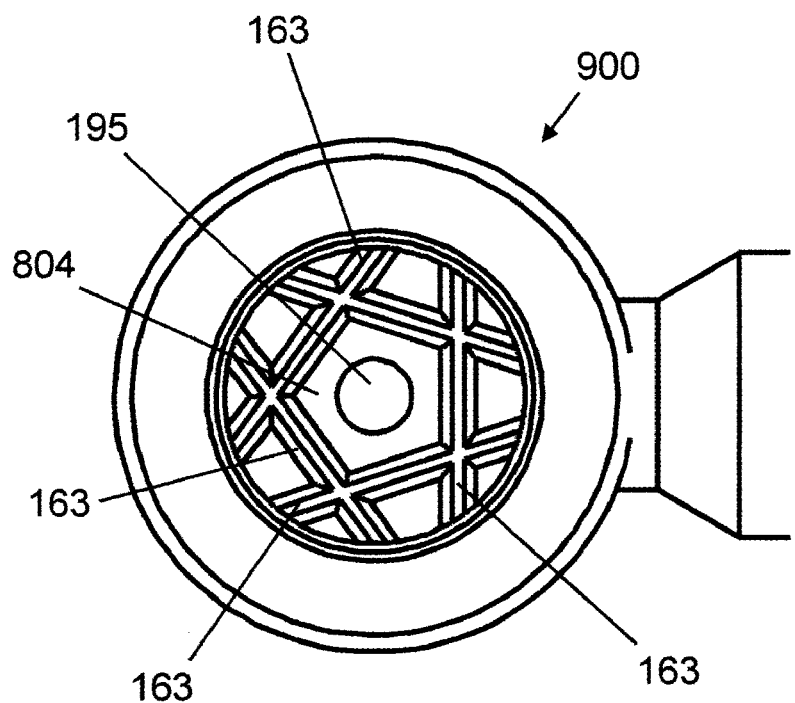
FIGS. 34 and 35 depict an expanded plan view of the distal portion of alternate embodiments formed in accordance with the principles of this invention.

FIG. 34 depicts an alternate embodiment in which the grooves are angularly oriented to each other so as to form a tubular portion around the aspirating port, the tubular portion having an outer surface that forms a regular polygon. Ablator 900 has grooves 163 are that are angulary oriented to one-another so as to form tubular portion 904 around aspiration port 195. Portion 904 forms a regular polygon when viewed in a plan view.

Figure 35:
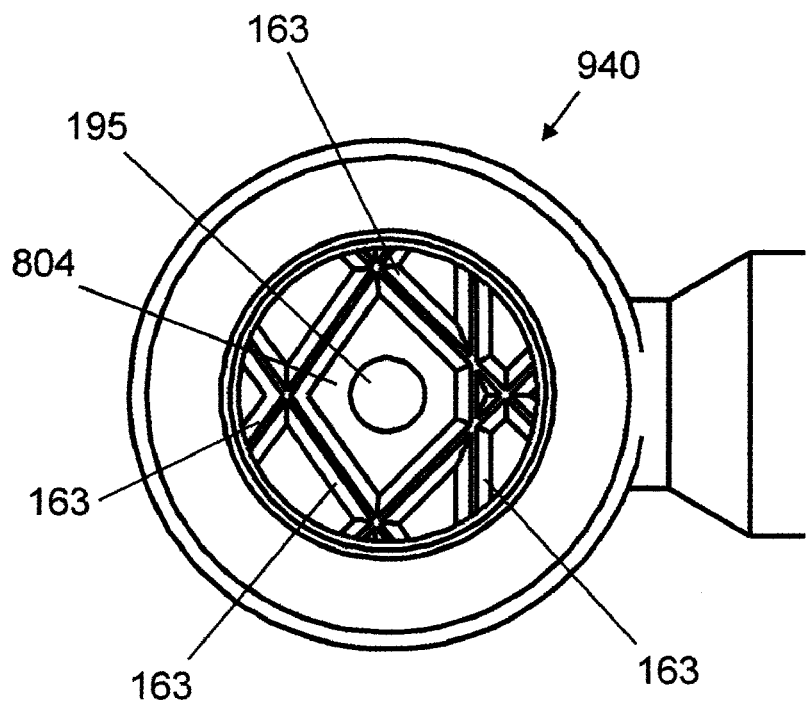

FIG. 35 depicts an alternate embodiment in which the grooves are angularly oriented to each other so as to form a tubular portion around the aspirating port, the tubular portion having an outer surface that forms an irregular polygon. Ablator 940 has grooves 163 that are angulary oriented to one-another so as to form tubular portion 904 around aspiration port 195. Portion 904 forms an irregular polygon when viewed in a plan view.

Other groove configurations may also be used in accordance with the present invention. For example, the grooves may have a curvilinear path so that the tubular portion formed has an irregular shape, the sides of the shape being curvilinear or linear, or a combination of linear and curvilinear. Any configuration which forms a tubular portion having a minimum wall thickness in the preferred range, and a maximum wall thickness in the preferred range may be used.

The high efficiency electrosurgical ablator 100, 600, 700, 800 of the present invention illustrated and described above may be employed in a variety of surgical medical procedures in the presence of an electrically conductive fluid to remove and/or modify a particular target tissue. Accordingly, the electrosurgical ablator 100, 600, 700, 800 of the present invention may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

The present invention has also equal applicability to surgical procedures where the target tissue is flooded with a natural conductive fluid of the human body, such as blood or lymphatic plasma, for example, which act as electrically conductive fluids. Nevertheless, an electrically conductive fluid introduced into the patient's body is preferred over blood because blood tends to coagulate at certain temperatures. In addition, the patient's blood or plasma may lack the necessary conductivity to adequately carry out the particular electrosurgical procedure desired.

Surgical procedures using the electrosurgical ablator 100, 600, 700, 800 of the invention include introducing the electrode assembly in close proximity to the surgical site through an artificial conduit or a cannula, or through a natural conduit which may be in an anatomical body cavity or space or one created surgically. For the purposes of the present invention, the terms "close proximity" and "proximity" are defined as "in contact with" or "at a distance of about 0.1 to about 10 millimeters." The cavity or space may be distended during the procedure using a fluid or may be naturally held open by anatomical structures. In addition, the surgical site may be bathed in a continuous flow of conductive fluid, such as saline solution, to fill and distend the cavity. The procedures may include simultaneous viewing of the site via an endoscope or using an indirect visualization means.

Figure 33:
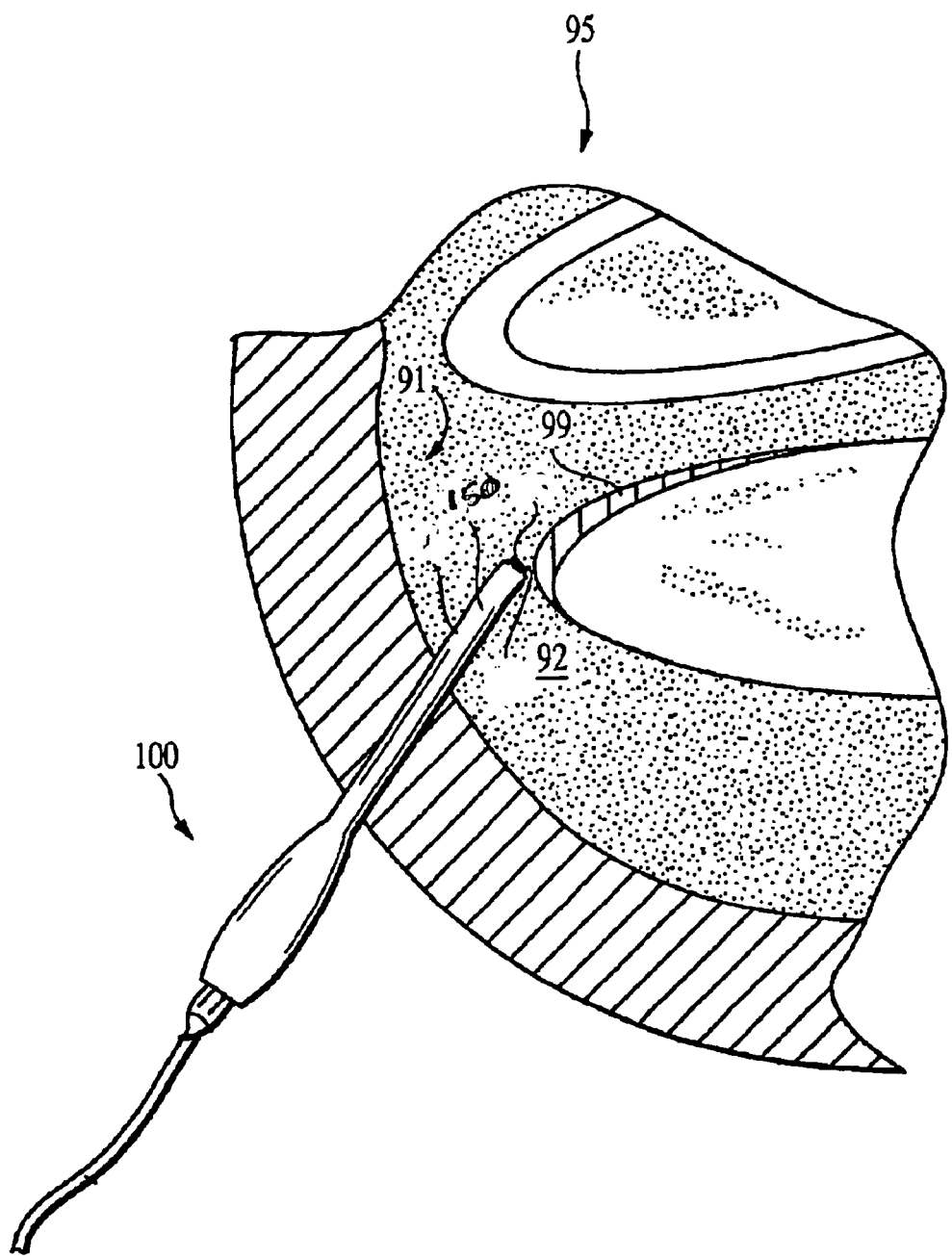
FIG. 33 is a schematic cross-sectional view of a knee joint undergoing an electrosurgical procedure employing an electrosurgical electrode of the present invention.

To better illustrate an exemplary surgical procedure conducted with the electrosurgical ablator 100 of the present invention, reference is now made to FIG. 33, which illustrates a schematic cross-sectional view of a knee joint region 95. The knee joint region 95 of FIG. 33 may undergo an arthroscopic procedure, for example, with electrosurgical ablator 100 fabricated according to the present invention. As known in the art, an endoscope (not shown) may be provided at one end with the distal active electrode piece 150 having aspiration tube 190, and then introduced into knee cavity 92 (FIG. 33) containing electrically conductive fluid 91 (FIG. 33) and in close proximity to target tissue 99 (FIG. 33). If the target tissue 99 of the knee joint region 95 is a damaged meniscus, for example, then target tissue 99 may undergo a partial or complete electrosurgical meniscectomy using active electrode 150. Alternatively, the endoscope may be introduced separately from the electrosurgical electrode, via separate access means in a surgical technique commonly known as triangulation. In any event, knee cavity 92 may be distended during the arthroscopic procedure using electrically conductive fluid 91, so that target tissue 99 may be bathed in a continuous flow of conductive fluid 91, which may be preferably a saline solution.

Once distal active electrode 150 is positioned in the proximity of the target tissue 99 and the target tissue 99 is submerged in the electrically conductive fluid 91, the electrosurgical probe is energized by the electrosurgery power supply. The power supply delivers radio frequency energy, typically in the range of 100 kHz to 3 MHz, through a cable system to the electrosurgical electrode 100 and further to the distal active electrode 150.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. An electrosurgical ablator comprising:
    a shaft having a proximal portion forming a handle and a tissue-contacting distal portion having an electrically conductive tip; and
    at least one active electrode located at or near said electrically conductive tip, the at least one active electrode comprising a plurality of electrically conductive protuberances spaced from each other and defining a plurality of recesses therebetween, said recesses characterized as having a bottom surface and a top surface, wherein said conductive tip further comprising a centrally located aspiration means comprising an aspirating port and an elevated wall extending above the bottom surface of said recesses and surrounding the entire perimeter of said aspirating port to thereby separate the aspirating port from adjacent recesses and reduce flow of fluid from the recesses directly into the aspirating port.

2. The electrosurgical ablator of claim 1, wherein the protuberances have a cross-sectional shape selected from the group consisting of rectangular, square, circular, trapezoidal, triangular, hexagonal and ellipsoidal shape, and a combination of such shapes.

3. The electrosurgical ablator of claim 1, wherein the aspiration means is integral with the active electrode.

4. The electrosurgical ablator of claim 1, wherein the aspiration means is provided as a separate component from the active electrode.

5. An electrosurgical system for the electrosurgical treatment of tissue immersed in a conductive fluid comprising:
    a power supply source; and
    the electrosurgical ablator of claim 1.

6. The electrosurgical ablator of claim 1, wherein the wall surrounding the aspiration port comprises a tubular member.

7. The electrosurgical ablator of claim 6, wherein the aspirating port is in communication with a vacuum source.

8. The electrosurgical ablator of claim 6, wherein the tubular member comprises a material which is similar to that of the plurality of protuberances.

9. The electrosurgical ablator of claim 6, wherein the tubular member comprises a material which is different from that of the plurality of protuberances.

10. The electrosurgical ablator of claim 6, wherein the tubular member has a distal transverse surface, and the plurality of protuberances have a distal transverse surface, the distal transverse surface of the tubular member being about equal in height with the distal transverse surface of the protuberances.

11. The electrosurgical ablator of claim 6, wherein the tubular member has a distal transverse surface, and the plurality of protuberances have a distal transverse surface, wherein the distal transverse surface of the tubular member protrudes above the distal transverse surface of the protuberances.

12. The electrosurgical ablator of claim 6, wherein the tubular member has a distal transverse surface, and the plurality of protuberances have a distal transverse surface, wherein the distal transverse surface of the tubular member is recessed below the most distal transverse surface of the protuberances.

13. The electrosurgical ablator of claim 6, wherein the tubular member has a cross-sectional shape selected from the group consisting of rectangular, square, circular, trapezoidal, triangular, hexagonal and ellipsoidal shape, and a combination of such shapes.

14. The electrosurgical ablator of claim 6, wherein the tubular member has a cross-sectional shape that is a regular polygonal shape.

15. The electrosurgical ablator of claim 6, wherein the tubular member has a cross-sectional shape that is an irregular polygonal shape.

16. The electrosurgical ablator of claim 6, wherein the protuberances have a circular cross-sectional shape and are concentric with the tubular member.

17. The electrosurgical ablator of claim 2, wherein the protuberances comprise an array of elevated cylinders concentrically disposed about the tubular member.

18. The electrosurgical ablator of claim 6, wherein the protuberances comprise a plurality curved ribs that define a corresponding plurality of circular grooves concentrically disposed about the tubular member.

19. The electrosurgical ablator of claim 6, wherein the protuberances comprise a plurality of elevated ribs that define a corresponding plurality of grooves.

20. The electrosurgical ablator of claim 19, wherein the ribs and grooves are substantially linear.

21. The electrosurgical ablator of claim 19, wherein the ribs and grooves form a curvilinear path.

22. A method of conducting an electrosurgical procedure comprising the steps of:
   providing the electrosurgical ablator of claim 1;
   positioning the active electrode of said ablator in the proximity of a tissue to be treated in the presence of an electrically conductive fluid;
   applying a high frequency voltage to the active electrode to generate an electric field adjacent said metallic tip;
   providing suction through the aspirating member of said ablator; and
   effecting ablation of at least a portion of the tissue to be treated.

23. The method of claim 22, wherein the plurality of protuberances have a distal surface, and wherein at least a portion of the wall of the aspirating member protrudes above the distal surface of the protuberances.

24. The method of claim 22, wherein the plurality of protuberances have a distal surface, and wherein the aspirating member is recessed below the distal surface of the plurality of protuberances.

25. The method of claim 22, wherein the aspirating member is concentric with at least one of the plurality of protuberances.

\* \* \* \* \*

UNITED STATES PATENT AND TRADEMARK OFFICE
CERTIFICATE OF CORRECTION

PATENT NO.         : 7,837,683 B2                                   Page 1 of 1
APPLICATION NO.    : 11/431515
DATED              : November 23, 2010
INVENTOR(S)        : Yuval Carmel et al.

It is certified that error appears in the above-identified patent and that said Letters Patent is hereby corrected as shown below:

At column 2, line 18, please correct the word "artroscopic" to correctly read --arthroscopic--.

At column 12, lines 9-10, please correct the phrase "a plurality of electrically conductive protuberances" to correctly read "a plurality of discrete electrically conductive elevated protuberances".

At column 12, lines 12-13, please correct the phrase "wherein said conductive tip further comprising" to more appropriately read "wherein said conductive tip further comprises".

Signed and Sealed this
Fifteenth Day of March, 2011

David J. Kappos
*Director of the United States Patent and Trademark Office*